US011739841B2

(12) United States Patent
Slaby et al.

(10) Patent No.: US 11,739,841 B2
(45) Date of Patent: Aug. 29, 2023

(54) INFUSION PUMP DOOR SEAL FOR VERTICAL INTRAVENOUS TUBES

(71) Applicants: Baxter International Inc., Deerfield, IL (US); Baxter Healthcare SA, Glattpark (CH)

(72) Inventors: Jiri Slaby, Buffalo Grove, IL (US); Mohammad Ali Jamnia, Pleasant Prairie, WI (US); Steve Pippin, Libertyville, IL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 73 days.

(21) Appl. No.: 16/871,534

(22) Filed: May 11, 2020

(65) Prior Publication Data

US 2020/0271226 A1    Aug. 27, 2020

Related U.S. Application Data

(63) Continuation of application No. 15/855,536, filed on Dec. 27, 2017, now Pat. No. 10,648,564.
(Continued)

(51) Int. Cl.
*F16J 15/10* (2006.01)
*A61M 5/142* (2006.01)
(Continued)

(52) U.S. Cl.
CPC ........ *F16J 15/104* (2013.01); *A61M 5/14228* (2013.01); *F04B 53/16* (2013.01);
(Continued)

(58) Field of Classification Search
CPC .... A61M 2205/0216; A61M 2205/121; A61M 5/14228; A61M 5/14212; A61M 5/142;
(Continued)

(56) References Cited

U.S. PATENT DOCUMENTS

| 5,823,746 A | 10/1998 | Johnson |
| 5,868,712 A * | 2/1999 | Briggs ................ A61M 5/365 |
| | | 417/63 |

(Continued)

FOREIGN PATENT DOCUMENTS

| EP | 2712653 | 4/2014 |
| EP | 2716312 | 4/2014 |
| WO | 2011121923 | 10/2011 |

OTHER PUBLICATIONS

Colombian Office Action, Application No. NC2019/0007743 dated Feb. 18, 2021—11 pages.
(Continued)

*Primary Examiner* — Jason E Flick
(74) *Attorney, Agent, or Firm* — K&L Gates LLP

(57) ABSTRACT

An infusion pump for delivering an intravenous ("IV") fluid includes a housing comprising an actuation area that engages a portion of an IV tube. The actuation area includes a first end that receives the IV tube from a fluid container and a second end that provides the IV tube to a patient. The housing also includes a seal section located along a perimeter of at least a portion of the actuation area. The seal section includes a gasket rib positioned along the seal section and a tube channel configured to cradle the IV tube. The example infusion pump also includes a door connected to the housing and configured to engage the gasket rib to enclose the actuation area of the housing.

17 Claims, 16 Drawing Sheets

Related U.S. Application Data

(60) Provisional application No. 62/440,755, filed on Dec. 30, 2016.

(51) Int. Cl.
*F04B 53/16* (2006.01)
*F04B 43/12* (2006.01)

(52) U.S. Cl.
CPC .............. *A61M 2205/0216* (2013.01); *A61M 2205/121* (2013.01); *F04B 43/12* (2013.01)

(58) Field of Classification Search
CPC ......... A61M 5/168; F04B 43/12; F04B 53/16; F04B 43/00; F04B 43/08; F04B 53/00; F16J 15/104; F16J 15/00; F16J 15/002; F16J 15/05
See application file for complete search history.

(56) References Cited

U.S. PATENT DOCUMENTS

| | | |
|---|---|---|
| 6,007,941 A | 12/1999 | Hermann et al. |
| 6,261,262 B1 | 7/2001 | Briggs et al. |
| 6,629,955 B2 | 10/2003 | Morris et al. |
| 6,907,830 B2 | 6/2005 | Guinan et al. |
| 6,942,473 B2 | 9/2005 | Abrahamson et al. |
| 7,611,498 B2 | 11/2009 | Hasler |
| 7,935,081 B2 | 5/2011 | Flaker et al. |
| 8,096,628 B2 | 1/2012 | Ostrowski |
| 8,118,778 B2 | 2/2012 | Haylor et al. |
| 8,257,066 B2 | 9/2012 | Kasai et al. |
| 8,308,457 B2 | 11/2012 | Rotem et al. |
| 8,430,654 B2 | 4/2013 | Kasai et al. |
| 2006/0140798 A1 | 6/2006 | Kutsuzawa |
| 2009/0306592 A1 | 12/2009 | Kasai et al. |
| 2011/0318208 A1 | 12/2011 | Golder et al. |
| 2012/0078185 A1 | 3/2012 | Smith et al. |
| 2012/0101438 A1 | 4/2012 | Gagliardoni et al. |
| 2012/0238991 A1 | 9/2012 | Zhang et al. |
| 2014/0100526 A1 | 4/2014 | Ueda |
| 2014/0100536 A1 | 4/2014 | Ueda |
| 2014/0271247 A1 | 9/2014 | Abal |
| 2014/0276424 A1 | 9/2014 | Davis et al. |

OTHER PUBLICATIONS

International Preliminary Report on Patentability related to PCT/US2017/068552 dated Apr. 8, 2019—18 pages.
International Search Report International Application No. related to PCT/US2017/068552 dated Mar. 26, 2018.
Written Opinion of the International Application No. related to PCT/US2017/068552 dated Mar. 26, 2018.
Written Opinion of the Preliminary Examining Authority related to PCT/US2017/068552 dated Dec. 5, 2018.
European Patent Office Communication Appl. No. 21169124.1-1122—7 pages.
Colombian Office Action Application No. 15866 dated Oct. 8, 2021—6 pages.
Australian Examination Report No. 1 for Application No. 2017388222 dated May 31, 2022.

\* cited by examiner

INFUSION PUMP DOOR SEAL FOR VERTICAL INTRAVENOUS TUBES

PRIORITY CLAIM

The present application claims priority to and the benefit of U.S. patent application Ser. No. 15/855,536, filed on Dec. 27, 2017, now U.S. Pat. No. 10,648,564, which claims priority to and the benefit of U.S. Provisional Patent Application No. 62/440,755, filed on Dec. 30, 2016, the entirety of which are incorporated herein by reference and relied upon.

BACKGROUND

Infusion pumps, including large volume pumps ("LVP's") are designed to move fluid through an intravenous ("IV") line from a fluid supply to a patient. The infusion pumps move the fluid through the IV line with one or more actuator that applies a force to a portion of the line. The rate at which a fluid is moved is based on a frequency at which the force is applied to the IV line. It is common for infusion pumps to use a door or similar mechanism to secure a portion of the IV line in contact with the actuators. Other known pumps require the use of specialized IV line sets that are integrated with tube-carrying cassettes or over-molds that are mated with pump actuators.

An issue with known infusion pumps is the seepage of containments (e.g., dust, moisture, fluid container leaks, etc.) into the actuator area of the infusion pump behind the door. In many instances, a small gap exists between an edge of the door and the infusion pump casing, enabling the contaminants to enter the actuation area. Gaps are also present around the IV line where it passes either through the door or the pump casing adjacent to the door to reach an infusion container. The gaps may be intentional and designed into the infusion pumps to reduce stress placed on the IV lines or to prevent the IV lines from occluding. Unfortunately, contaminants may affect actuator operation, resulting in more frequent maintenance and/or cleaning.

SUMMARY

The present disclosure involves an infusion pump that delivers intravenous ("IV") fluids to a desired source, such as a human being or animal (e.g., patient). The infusion pump includes an improved door seal. The example door seals of the present disclosure are configured to enclose or protect an actuation area of an infusion pump from contaminants. The positioning of the seals with respect to the door isolates an actuation area independent of manufacturing tolerance variations of the overall door and/or pump casing. In an embodiment, a seal is formed inside of a door's edges, which relaxes the tolerance ranges of the pump housing and door, thereby reducing manufacturing costs. Accordingly, the example seal configurations disclosed herein are agnostic of a door position and tolerance stack-up. Further, the example configurations disclosed herein are operable with conventional IV tubes, so that specialized IV tubes, receptacles, cartridges, or additional parts are not needed. Materials for the different components of the infusion pumps discussed below may include metal, plastic, rubber and combinations thereof.

Aspects of the subject matter described herein may be useful alone or in combination with one or more other aspect described herein. Without limiting the foregoing description, in a first aspect of the present disclosure, an infusion pump for delivering an intravenous ("IV") fluid includes a housing including an actuation area configured to engage a portion of an IV tube, the actuation area including a first end to receive the IV tube from a fluid container and a second end to provide the IV tube to a patient and a seal section located along a perimeter of at least a portion of the actuation area. The example seal section includes a gasket rib positioned along the seal section and a tube channel configured to cradle the IV tube. The infusion pump also includes a door connected to the housing and configured to engage the gasket rib to enclose the actuation area of the housing. The door includes at least one of a recess section configured to align with the tube channel when the door is closed, the recess section configured to cradle the IV tube such that the recess section and tube channel together enclose the IV tube, or a channel relief lip configured to engage the IV tube entering the door.

In accordance with a second aspect of the present disclosure, which may be used in combination with any other aspect listed herein unless stated otherwise, the seal section includes a tube guidance section located between the tube channel and the actuation area, the tube guidance section configured to cradle the IV tube, causing the IV tube to bend for a desired orientation in the actuation area.

In accordance with a third aspect of the present disclosure, which may be used in combination with any other aspect listed herein unless stated otherwise, the tube channel includes a surface that is at least one of (i) smooth, (ii) course ribbed, or (iii) fine ribbed.

In accordance with a fourth aspect of the present disclosure, which may be used in combination with any other aspect listed herein unless stated otherwise, the gasket rib includes at least one of (i) a single rib, or (ii) at least two ribs in parallel.

In accordance with a fifth aspect of the present disclosure, which may be used in combination with any other aspect listed herein unless stated otherwise, the gasket rib includes an elastomeric material.

In accordance with a sixth aspect of the present disclosure, which may be used in combination with any other aspect listed herein unless stated otherwise, the gasket rib is molded with the housing.

In accordance with a seventh aspect of the present disclosure, which may be used in combination with any other aspect listed herein unless stated otherwise, the cradling of the IV tube by the recess section and the tube channel causes the IV tube to bend for a desired orientation under a roof of the door.

In accordance with an eighth aspect of the present disclosure, which may be used in combination with any other aspect listed herein unless stated otherwise, the roof further includes a rib located on a side of the roof that is configured to engage a channel of the housing that is adjacent to the actuation area, the engagement of the rib with the channel preventing the roof from bowing.

In accordance with a ninth aspect of the present disclosure, which may be used in combination with any other aspect listed herein unless stated otherwise, the channel relief lip includes at least one rib configured to cause at least one region in the IV tube to remain uncollapsed at the location where the IV tube is bent.

In accordance with a tenth aspect of the present disclosure, which may be used in combination with any other aspect listed herein unless stated otherwise, the first end is a top end of the actuation area and the second end is a bottom end of the actuation area.

In accordance with an eleventh aspect of the present disclosure, which may be used in combination with any other aspect listed herein unless stated otherwise, the gasket rib includes a tube window positioned adjacent to the first end of the actuation area configured to receive the IV tube.

In accordance with a twelfth aspect of the present disclosure, which may be used in combination with any other aspect listed herein unless stated otherwise, the tube channel is located at the tube window.

In accordance with a thirteenth aspect of the present disclosure, which may be used in combination with any other aspect listed herein unless stated otherwise, the door includes a roof configured to extend over the housing at the first end of the actuation area, the roof including the at least one of the recess section or the channel relief lip.

In accordance with a fourteenth aspect of the present disclosure, which may be used in combination with any other aspect listed herein unless stated otherwise, the door is hingedly connected to the housing.

In accordance with a fifteenth aspect of the present disclosure, which may be used in combination with any other aspect listed herein unless stated otherwise, an infusion pump for delivering an intravenous ("IV") fluid includes a housing including an actuation area configured to engage a portion of an IV tube, the actuation area including a first end to receive the IV tube from a fluid container and a second end to provide the IV tube to a patient, and a seal section located along a perimeter of at least a portion of the actuation area. The example seal section includes a gasket rib positioned along the seal section, and a tube channel configured to cradle the IV tube. The infusion pump also includes a door connected to the housing and configured to engage the gasket rib to enclose the actuation area of the housing.

In accordance with a sixteenth aspect of the present disclosure, which may be used in combination with any other aspect listed herein unless stated otherwise, the door includes a roof configured to extend over the housing at the first end of the actuation area, the roof including the at least one of a recess section or a channel relief lip.

In accordance with a seventeenth aspect of the present disclosure, which may be used in combination with any other aspect listed herein unless stated otherwise, the cradling of the IV tube by the tube channel causes the IV tube to bend for a desired orientation under the roof.

In accordance with an eighteenth aspect of the present disclosure, which may be used in combination with any other aspect listed herein unless stated otherwise, the roof further includes a rib located on a side of the roof that is configured to engage a channel of the housing that is adjacent to the actuation area, the engagement of the rib with the channel preventing the roof from moving upwards.

In accordance with a nineteenth aspect of the present disclosure, which may be used in combination with any other aspect listed herein unless stated otherwise, the door includes at least one of a recess section configured to align with the tube channel when the door is closed, the recess section configured to cradle the IV tube such that the recess section and tube channel together enclose the IV tube, or a channel relief lip configured to engage the IV tube entering the door.

In accordance with a twentieth aspect of the present disclosure, which may be used in combination with any other aspect listed herein unless stated otherwise, the channel relief lip includes at least one rib configured to cause at least one region in the IV tube to remain uncollapsed at the location where the IV tube is bent.

In accordance with a twenty-first aspect of the present disclosure, any of the structure and functionality illustrated and described in connection with FIGS. 6A to 36 may be used in combination with any of the structure and functionality illustrated and described in connection with any of the other of FIGS. 6A to 36 and with any one or more of the preceding aspects.

In light of the aspects above and the disclosure herein, it is accordingly an advantage of the present disclosure to provide an infusion pump that has relaxed component mating tolerances.

It is another advantage of the present disclosure to provide an infusion pump that effectively prevents fluid and other contaminants from entering a housing of the pump.

It is a further another advantage of the present disclosure to provide an infusion pump that may operate with standard, non-specialized pump sets and tubing.

The advantages discussed herein may be found in one, or some, and perhaps not all of the embodiments disclosed herein. Additional features and advantages are described herein, and will be apparent from the following Detailed Description and the figures.

DETAILED DESCRIPTION

The present disclosure relates in general to an infusion pump apparatus that includes a door roof and gasket seal configured to prevent entrance of environmental contaminants into an intravenous ("IV") tube actuation area. As described in more detail below, an infusion pump door in an embodiment includes a roof with a recess section configured to cradle or otherwise accept an IV tube. In addition, the infusion pump may include a gasket seal configured to contact at least the door roof when the door is in a closed position. The gasket seal includes a tube channel and window that are positioned opposite from the recess in the roof. The tube channel and window are configured to cradle or otherwise contact an IV tube. The cradling of the IV tube by the tube channel, window, and roof recess substantially encloses the IV tube underneath the roof. When combined with the gasket seal, the enclosure of the IV tube creates a substantially impenetrable barrier against environmental contaminants entering an IV tube actuation area of the infusion pump.

Reference is made throughout to infusion pumps that are configured to receive IV tubes in a vertical orientation. In other words, the infusion pumps receive an IV tube in a top section. However, it should be appreciated that in other embodiments, the infusion pump seal disclosed herein may be provided to receive horizontally (or other desired angle) orientated IV tubes. In the other embodiments, the IV tube enters a side of the infusion pump. In an embodiment, the infusion pump may be oriented in different positions for operation, such that the tube may be disposed differently for different procedures.

Likewise, the infusion pumps disclosed herein have general vertically orientated actuators for pumping fluid through the IV tubes. However, in other embodiments, the actuators may be positioned in a horizontal (or other desired angle) orientation. It should be appreciated that the orientation of the actuators may not necessarily correspond to the orientation of an IV tube entering the infusion pump. For example, an infusion pump may receive an IV tube in a horizontal orientation but have the actuators be aligned in a vertical orientation. Again, the actuators may be oriented differently for different procedures.

The example infusion pump seal disclosed herein overcomes limits of known systems (discussed briefly below) that permit environmental contaminants to enter an actuation area. In addition, the example infusion pump seal disclosed herein is configured to meet the IEC 60601 IPX2 requirement regarding fluid ingress. This standard requires that a home-based medical device be protected against the ingress of water drops falling vertically when the medical device is tilted at a 15° angle in different orientations. This includes tilting a medical device forward, backward, and sideways by 15°.

Figure 1:
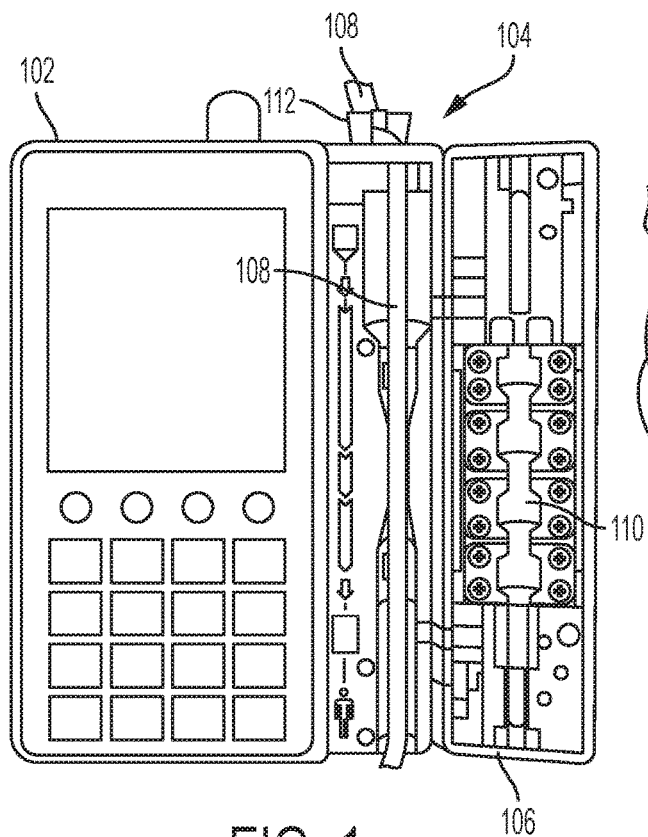
FIGS. 1 to 5 are various views of known infusion pumps that use different constructions to attempt to prevent environmental contamination of an actuation area.
Figure 2:
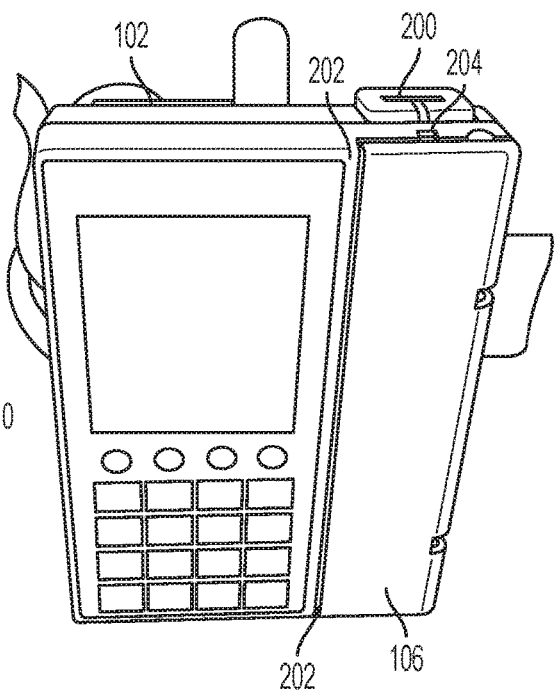
Figure 3:
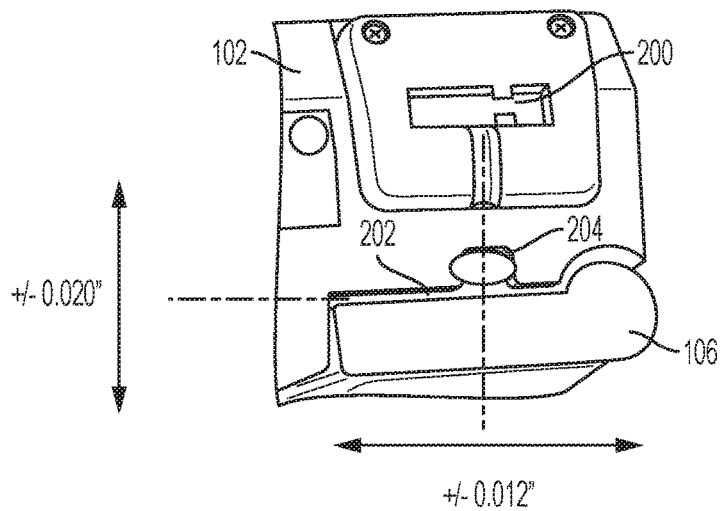
Figure 4:
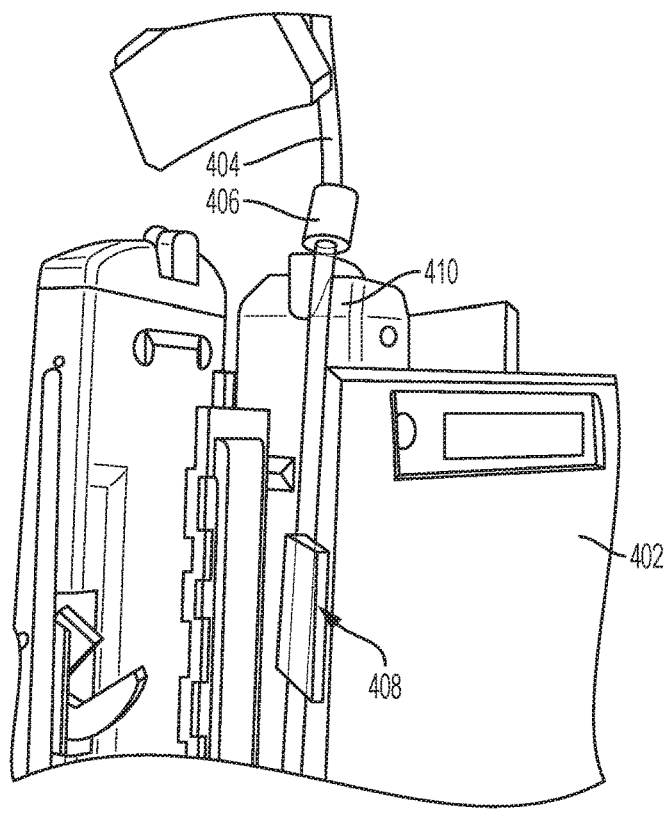
Figure 5:
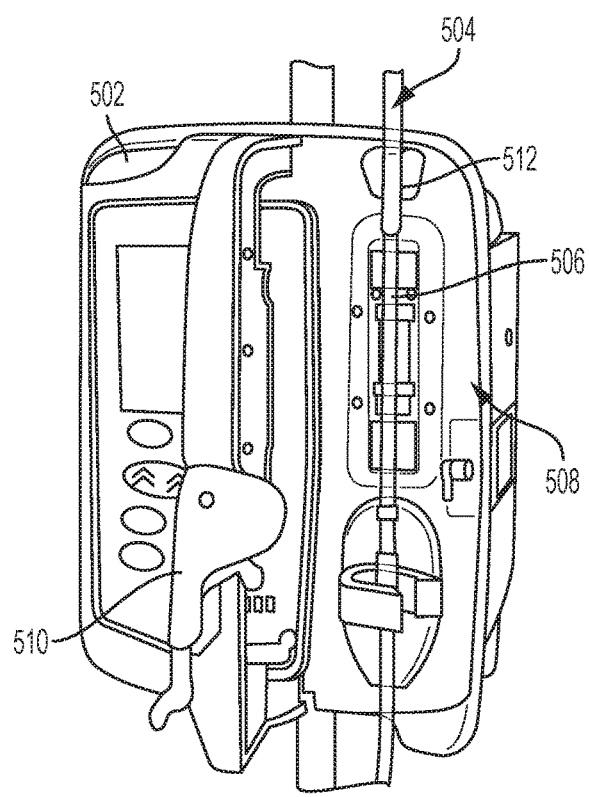

Referring now to the drawings, FIGS. 1 to 5 show diagrams of known infusion pumps that use different constructions to attempt to prevent environmental contamination of an actuation area. Specifically, FIGS. 1 to 3 show one infusion pump that attempts to minimize gaps at the door. By comparison, FIGS. 4 and 5 show infusions pumps that use custom overmolds or cartridges with IV tubes.

FIGS. 1 to 3 show diagrams of a known infusion pump 102 that includes an actuation area 104 enclosed by a door 106. An IV tube 108 is routed through the actuation area 104. In this example, actuators 110 are positioned on the door 106, which is shown in an open position in FIG. 1. Closure of the door 106 causes the actuators 110 to contact or be in close proximity to a portion of the IV tube 108 within the actuation area 104. The actuators 110 are controlled to sequentially push against the IV tube 108 to move or pump a fluid through the tube 108.

The known infusion pump 102 is configured such that the IV tube 108 is orientated vertically though the actuation area 104. The IV tube 108 at its top end of the actuation area 104 is connected to a fluid container. The IV tube 108 at its bottom end of the actuation area 104 is connected to a patient. The infusion pump 102 includes a clip 112 or slide clamp configured to connect to IV tube 108 at the top of infusion pump 102. Insertion of clip 112 into slot 200 (shown in FIGS. 2 and 3) causes door 106 to open. Clip 112 also causes occlusion of the IV tube 108 to prevent fluid flow while IV tube 108 is being loaded into the infusion pump 102. After IV tube 108 is secured in the actuator area 104, door 106 is closed and clip 112 is removed, thereby enabling fluid to flow through IV tube 108.

FIGS. 2 and 3 show the door 106 of the infusion pump 102 in a closed position. The example door 106 is configured to cover a portion of the actuation area 104. However, gaps 202 and 204 exist between the door 106 and corresponding casing on the infusion pump 102. Gaps 202 correspond to voids between edges of the door 106 and the casing of the infusion pump 102 along the edges of the door. Gap 204 corresponds to a void between the door 106 and the casing of the infusion pump 102 where the IV tube 108 enters the actuation area 104. As shown in FIG. 3, gaps 202 may be about 0.020 inch (0.5 mm), while gap 204 may be about 0.012 inch (0.3 mm).

The example gaps 202 may exist as a result of manufacturing tolerance allowances. For instance, the door 106 and housing of the infusion pump 102 may be injection molded separately. Allowance for large tolerance variability reduces manufacturing costs, but results in the gaps 202. In addition, the door 106 may have a wide positioning tolerance to ensure enclosure of the actuation area 104 through extended use while reducing manufacturing costs. Moreover, the aggressive environment in which the infusion pump 102 is operated prevents the use of some materials that may provide lower tolerance variability.

In addition, gap 204 is provided to enable the IV tube 108 to enter the actuation area 104 without pinching or occluding the IV tube 108. As shown in FIG. 1, the IV tube is bent in the location of the gap 204. The gap 204 enables the IV tube 108 to bend without restricting or cutting off fluid flow from an attached container.

The gaps 202 and 204, while relatively small, enable environmental contaminants to enter the actuation area 104. Over time, contaminants may accumulate in the actuation area 104 and affect operation of the actuators 110, including the positionability of the IV tube 108 in the actuation area 104. To prevent adverse operation, the actuation area 104 may have to be cleared or serviced regularly.

The gaps 202 and 204 also enable fluid from a fluid container to reach the actuation area 104 outside of the IV tube 108. For example, a fluid container may leak fluid when being connected to an IV tube. Leaked fluid from the container may spill onto the infusion pump 102, which is usually positioned directly under the container. The fluid may seep into the actuation area 104 through the gaps 202 and 204 and degrade or otherwise affect operation of the actuators 110.

FIGS. 4 and 5 show diagrams of other known infusion pumps that use overmolds or cassettes to prevent environmental contamination. As shown, the overmold or cassette includes features that seal or otherwise securely enclose an actuation area. For example, FIG. 4 shows an infusion pump 402 with an IV tube 404 containing an overmold 406. The overmold 406 includes a sleeve that encases the IV tube 404. The purpose of the overmold 406 is to enable the IV tube 404 to be enclosed at an entrance of actuation area 408 without a chance of the IV tube being compressed. The infusion pump 402 includes a receptacle 410 configured to connect to the overmold 406. As illustrated in FIG. 4, the connection between the overmold 406 and the receptacle 410 leaves few, if any gaps.

FIG. 5 shows a diagram of an infusion pump 502 configured to connect to an IV tube 504 that is included within a cartridge 506. The cartridge 506 is connected to an actuation area 508 of the infusion pump and is enclosed via door 510. The cartridge 506 includes a sleeve or clip 512 at an entrance to the actuation area 508. The clip 512 is similar to the overmold 406 of FIG. 4 and reduces or eliminates a gap between the door 510 and a housing of the pump 502. The clip 512 may be made from an elastic material that enables the door 510 to engage the cartridge 506 without compressing the IV tube 504.

An issue with the known infusion pumps 402 and 502 of FIGS. 4 and 5, respectively, is that custom IV tubes have to be created with the overmold 406 or the cartridge 506. In some instances, the overmold 406 and/or cartridge 506 may comprise a majority of a cost of an IV tube. Such solutions are not desirable for cost reasons, which is especially significant in developing counties. Further, the overmolds 406 and cartridge 506 are unique to its associated pump. A change among pump models or model configuration may require a purchase of new corresponding IV tubes, rendering old tubes still in stock useless.

Other known infusion pumps seal an actuation area using an elastomeric foil. For instance, an area around actuators may include the elastomeric foil. An opposite section on a door is configured to engage and press against the foil around the actuators, creating a tight enclosure, while leaving a slight opening for an IV tube. Unfortunately, the elastomeric foil degrades over time, leading to frequent maintenance and costly replacement.

Still other known infusion pumps have a tube opening along a side section. These known pumps have vertically orientated finger-shaped actuators. As one can appreciate, installation of the IV tube is complex since an operator has to bend the tube inside the actuation area along a defined channel. In addition, the use of the channel and horizontal orientation of the IV tube prevents a seal from being used at an entrance of the actuation area. Otherwise, an IV tube may bend at the seal, potentially restricting fluid flow.

Further known infusion pumps include a foam band along a circumference of a door. The foam, however, degrades over time and requires frequent replacement, resulting in high maintenance costs. Further, some foams may become contaminated over time, resulting in contaminants reaching an actuation area.

Example Door Seal for Infusion Pumps

The example door seals of the present disclosure are configured to enclose or protect an actuation area of an infusion pump from contaminants. The positioning of the seals with respect to the door isolates an actuation area independent of manufacturing tolerance variations of the overall door and/or pump casing. In an embodiment, a seal is located inward from a door's edges, which relaxes the tolerance ranges of the pump housing and door, thereby reducing manufacturing costs. Accordingly, the example seal configurations disclosed herein are agnostic of a door position and tolerance stack-up. Further, the example configurations disclosed herein are operable with conventional IV tubes, so that specialized IV tubes, receptacles, cartridges, or additional parts are not needed. Materials for the different components of the infusion pumps discussed below may include metal, plastic, rubber and combinations thereof.

Figure 6A:
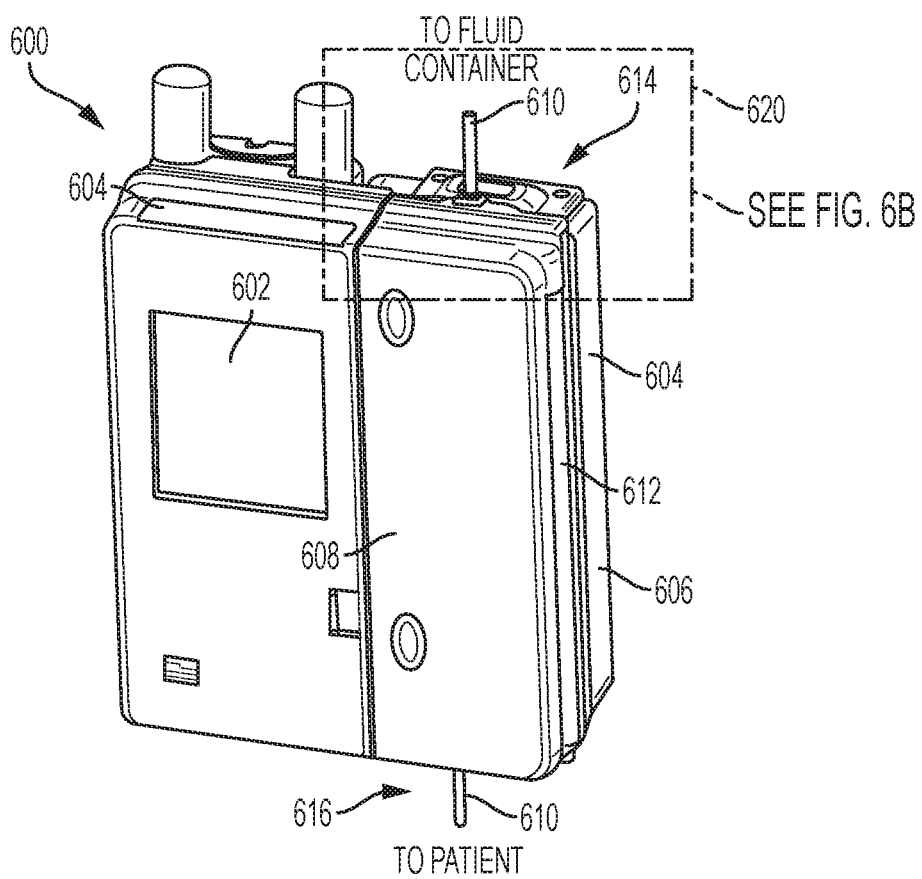
FIGS. 6A, 6B, 7A, and 7B are various views of an example infusion pump that includes a door seal section configured to reduce or prevent environmental contamination of an actuation area, according to an example embodiment of the present disclosure.
Figure 6B:
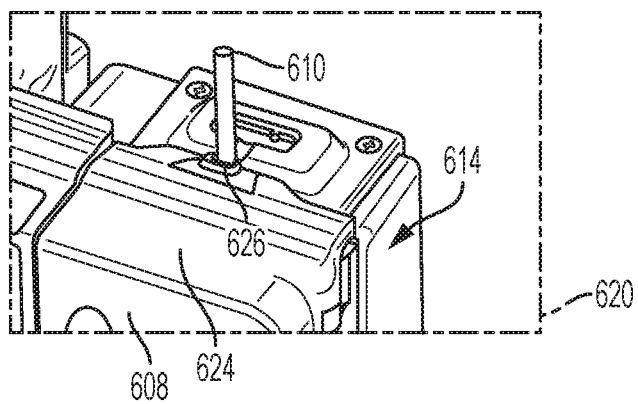
Figure 7A:
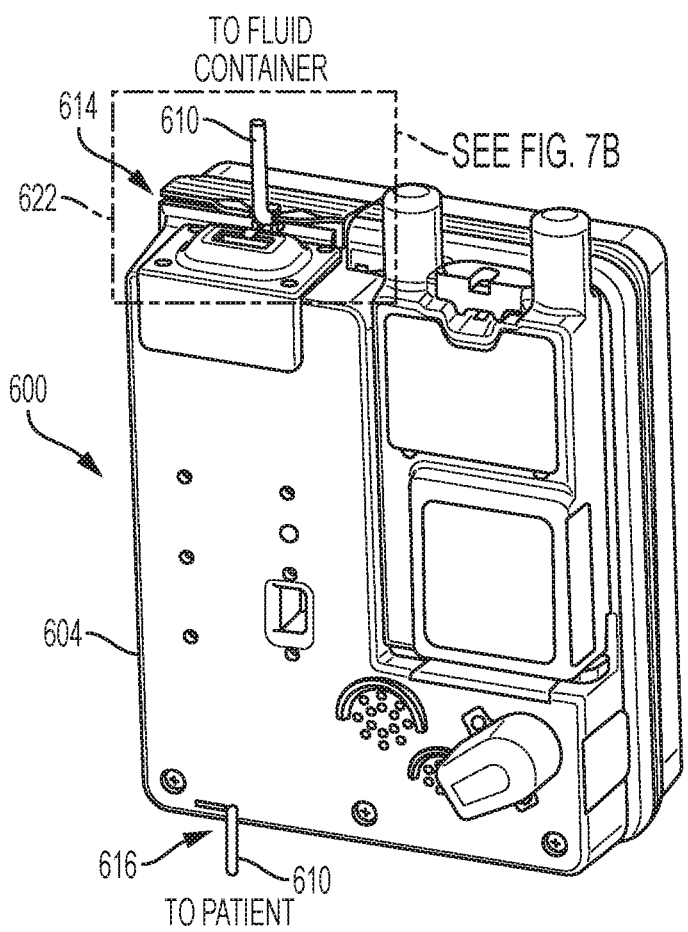
Figure 7B:
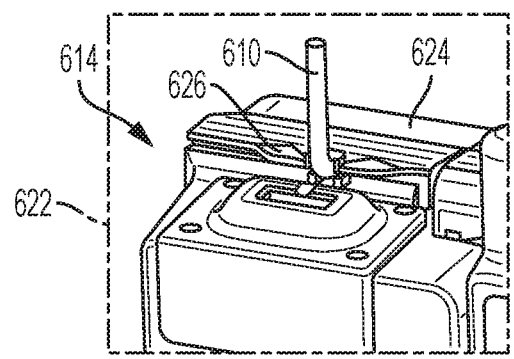

FIGS. 6A, 6B, 7A, and 7B show diagrams of an example infusion pump 600 including an embodiment of the disclosed door seal. FIGS. 6A and 6B show a front-perspective view, while FIGS. 7A and 7B show a rear-perspective view of the infusion pump 600. The example infusion pump 600 may include any pump capable of delivering an intravenous therapy to a patient via one or more IV tubes or line sets. Examples include a linear peristaltic pump, a large volume pump ("LVP"), an ambulatory pump, and/or a multi-channel pump, etc. A linear peristaltic pump uses a rotor to compress part of a tube while rotating. Often, one or more rollers of the rotor contact the tube for half a rotation. The compressed rotation causes a defined amount of fluid to pass through the tube. LVP's typically use one or more finger or arm to compress a portion of intravenous therapy ("IV") tube. The timing of the finger actuation on the tube causes constant or near constant movement of a fluid through the tube.

The example infusion pump 600 includes a display interface 602 to display pump information. The display interface 602 may also facilitate the programming of the pump 600 via a touch screen, membrane switch, combinations thereof, or other type of user interface. The infusion pump 600 in an embodiment also includes a housing 604 configured to enclose electronics and actuators, which are located within actuation area 606. The infusion pump 600 further includes a door 608, which is shown in FIGS. 6A and 6B in a closed position enclosing the actuation area 606. The example door 608 is configured (e.g., hinged) to open, thereby providing access to the actuation area 606. A clinician may open the door 608 to insert IV tube 610 into the actuation area 606 by, for example, placing the IV tube into one or more channel or connector that holds the IV tube in place for actuation.

The example door 608, in the illustrated embodiment, is connected to the housing 604 of the infusion pump 600 via one or more hinge 612. In the illustrated example, the hinges 612 are positioned on a side of the infusion pump 600, which causes the door 608 to swing away from the display interface 602. Such a configuration enables a clinician to install the IV tube 610 while still being able to view the interface 602. Otherwise, locating hinges between the door 608 and display interface 602 would cause the door 608 to open in the opposite direction, thereby obstructing the view of the interface 602.

As illustrated in FIGS. 6A, 6B, 7A, and 7B, the IV tube 610 enters (from a fluid flow standpoint) the infusion pump 600 at a top end 614 of the actuation area 606. The IV tube 610 at the top end 614 is connected to a fluid container, such as an IV bag. The IV tube 610 is generally orientated vertically above the top end 614 to the fluid container to take advantage of gravity and to allow air to collect at the top of an IV bag while introducing IV fluid into tube 610. The IV tube 610 exits (from a fluid flow standpoint) the infusion pump 600 at a bottom end 616 of the actuation area 606. The IV tube 610 at the bottom end 616 extends to its delivery destination, e.g., a patient.

Cutaways 620 and 622 show enlarged views of in an embodiment of the top end 614 of the actuation area, and of the infusion pump 600 in general. The cutaways 620 and 622 illustrate that the door 608 includes a roof 624, which is configured to cover an adjacent portion of the housing 604 in addition to the top end 614 of the actuation area 606. The roof 624 includes a channel relief lip 626 that aligns and/or secures the IV tube 610 at the entrance to the roof 624. The roof 624 and channel relief lip 626 are described in more detail below.

Figure 8:
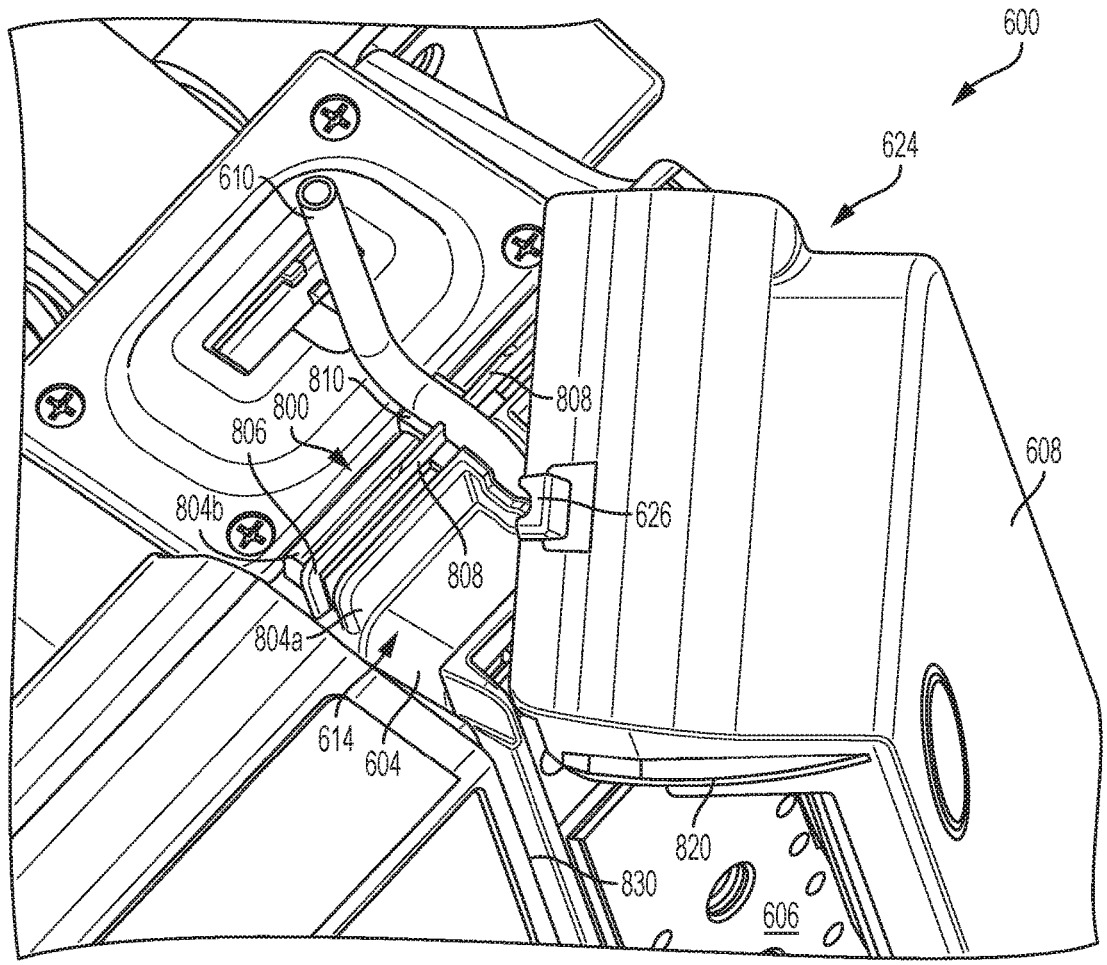
FIGS. 8 to 11 are various views of an enlarged view of seal section of the infusion pump of FIGS. 6A, 6B, 7A, and 7B, according to an example embodiment of the present disclosure.

FIG. 8 shows a diagram of an enlarged view of the top end 614 of the actuation area 606, according to an example embodiment of the present disclosure. In this embodiment, the door 608 is partially opened to expose the actuation area 606. As shown, the top end 614 of the actuation area 606 includes a portion of the housing 604 of the infusion pump 600. The top end 614 also includes a seal section 800, which when engaged with the roof 624 of the door 608, blocks or prevents contaminants from entering the actuation area 606.

The seal section 800 is positioned along a perimeter of the actuation area 606 at the top end 614. In an embodiment, the seal section 800 may also be positioned along a perimeter of the actuation area 606, including extending along the internal side vertically within the infusion pump 600. Additionally or alternatively, the seal section 800 may also be positioned along a perimeter of the actuation area 606 at its bottom end 616.

The seal section 800 in an embodiment includes ridges 804a and 804b configured to sandwich and/or support a gasket rib 806. The illustrated ridges 804a and 804b extend vertically from the housing 604 and may be made of the same material and/or be integrated with the housing 604. In some instances, the ridges 804a and 804b have the same heights and/or widths. In other instances, the ridges 804a and 804b have varying heights and/or widths. For example, the ridge 804a may include a lip or edge that extends further vertically than the other ridges.

The example gasket rib 806 is positioned to run along the seal section between the ridges 804a and 804b. In some instances, an end of the gasket rib 806 may extend from the ridges 804, as shown in FIG. 8. The gasket rib 806 may include an elastomeric material to help create a seal against the roof 624 when the door 608 is closed. The gasket rib 806 includes a tube window 808 positioned at the top end 614 adjacent to where the IV tube 610 is received into the actuation area 606. The tube window 808 may be integrated with the gasket rib 806, such that both are made of the same material. In other instances, the tube window 808 may be connected to the gasket rib 806. The tube window 808 in the illustrated embodiment extends vertically above the gasket rib 806 such that edges of the tube window 808 contact external sides of the IV tube 610. In some instances, the edges of the tube window 808 may be curved to conform to a curvature of the IV tube 610 to provide a secure connection without compressing the IV tube 610.

The gasket rib 806 may also include a tube channel 810 located at the tube window 808 and be configured to cradle, connect, or otherwise accept the IV tube 610. Similar to the tube window 808, the tube channel 810 may also be molded or made from the same material as the gasket rib 806. The tube channel 810 is configured to be placed on at least a portion of the ridges 804a and 804b. In some instances, the ridges 804a and/or 804b may include recesses or channels to accept the tube channel 810. In other examples, the ridges 804a and 804b are substantially flat, such that the IV tube 610 may be placed on top of the ridges 804 within the tube channel 810.

As shown in FIG. 8, the combination of the tube channel 810 and the tube window 808 encloses the external sides and bottom half of the IV tube 610. The elastomeric nature of the tube window 808 and channel 810 enables the IV tube 610 to be secured without causing compression or fluid occlusion. Further, connection of the IV tube 610 to the tube window 808 and channel 810 causes the connected IV tube 610 to be placed in a horizontal orientation, which enables the roof 624 to close over the top end 614 without scratching, pulling, or otherwise mechanically affecting the IV tube 610.

Also shown in FIG. 8, the example roof 624 may extend inwardly to cover the top end 614 of the actuation area 606. The roof 624 may include the channel relief lip 626 to engage or connect the vertically orientated IV tube 610. The roof 624 also includes a roof rib 820 located on a side of the roof 624. The example roof rib 820 is configured to engage a corresponding channel 830 in the housing 604 to prevent, for example, the roof 624 from bowing, being pulled, and/or or lifted upwards. In some examples, the roof rib 820 may be omitted.

Figure 9:
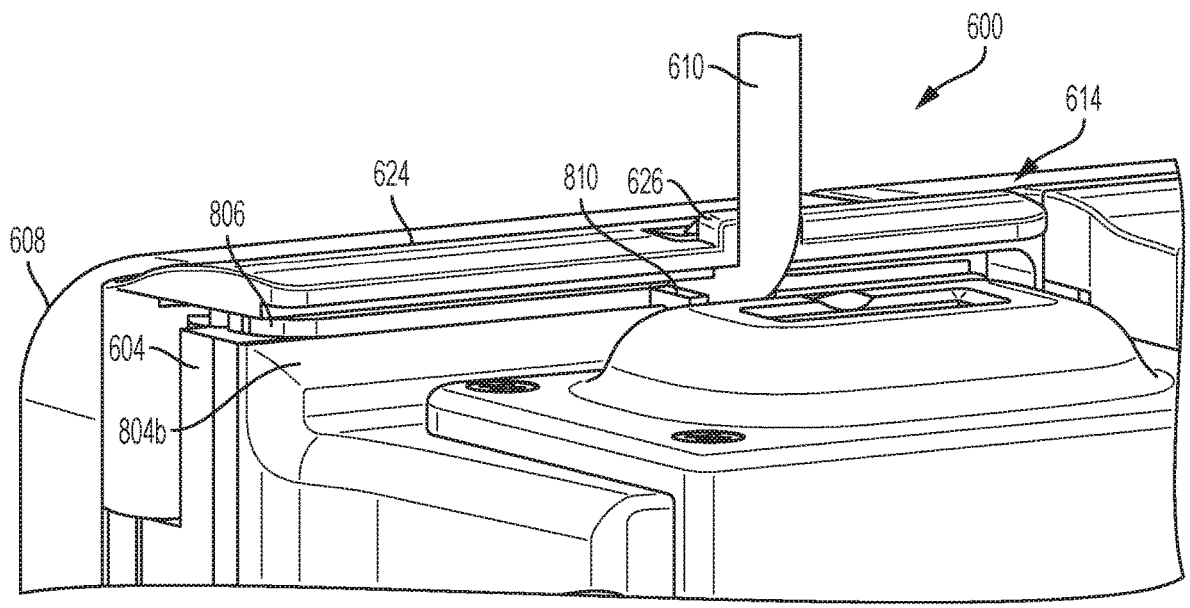

FIG. 9 shows a diagram of an embodiment of the door 608 moved to a closed position to enclose the actuation area 606. In this example, an underside of the roof 624 engages the gasket rib 806, thereby creating a seal between the roof 624 and the housing 604 of the infusion pump 600 and preventing contaminants from entering the actuation area 606 through any gaps between the door 608 and the housing 604. In addition, an underside of the roof 624 in an embodiment contacts or cradles a top half of the horizontally orientated section of the IV tube 610 at the same location where the tube window 808 and tube channel 810 engage the IV tube 610. Together, the underside of the roof 624, the tube window 808, and the tube channel 810 in an embodiment enclose an entire external circumference of the IV tube 610, which prevents contaminants from entering the actuation area 606 along any potential gaps around the IV tube 610. At the same time, the engagement of IV tube 610 is constructed so as not to cause compression and possible fluid occlusions.

Figure 10:
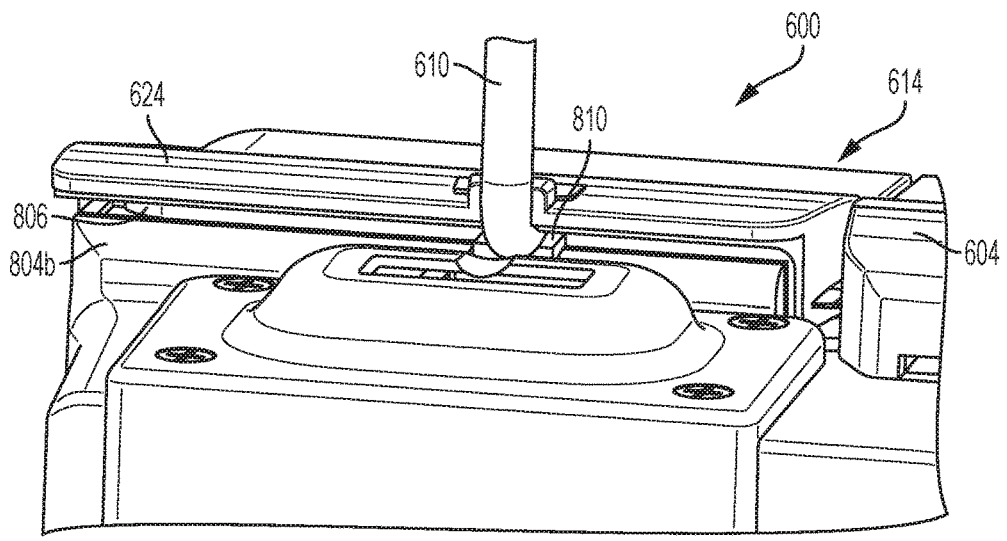
Figure 11:
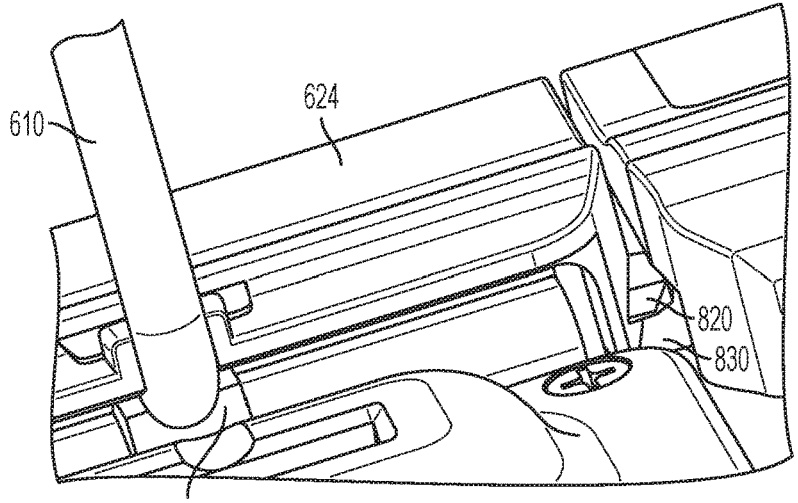

FIGS. 10 and 11 show diagrams of different perspective views of the door 608 example shown in FIG. 9. As shown in these figures, a seal is formed in an embodiment between the roof 624 and the housing 604 via the gasket rib 806. FIG. 11 also shows the roof rib 820 engaged with channel 830 of the housing 604 to prevent, for example, the roof 624 from bowing. As shown in FIGS. 9 to 11, the tolerances between the door 608, roof 624, and housing 604 are allowed greater variability because the seal occurs at the gasket rib 806 underneath the roof 624 and/or on an inside of the door 608. In other words, the gasket rib 806 allows for gaps of varying widths to occur between the door 608 and the housing 604 without allowing contamination of the actuation area 606. The seal formed between the gasket rib 806 and the roof 624 and/or the door 608 accordingly provides a tolerance agnostic solution that enables a door 608 and housing 604 to have a wide tolerance range because the seal quality is not sensitive or based on the position of the door 608 over the seal or relative to corresponding features or sections of the housing 604. Further, as shown in FIGS. 9 to 11, the seal in an embodiment is compatible with standard (unmodified) IV tubes, which is more cost efficient.

Figure 12:
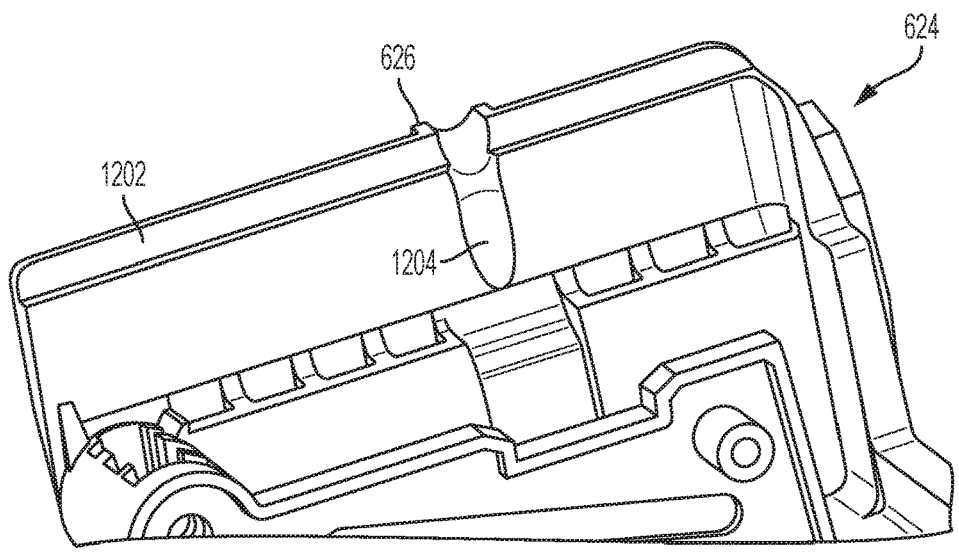
FIG. 12 is a perspective view of a roof of a door of the infusion pump of FIGS. 6A, 6B, 7A, and 7B, according to an example embodiment of the present disclosure.

FIG. 12 shows a diagram of an underside of the roof 624, according to an example embodiment of the present disclosure. As discussed above, the roof 624 includes channel relief lip 626 to engage or otherwise contact an IV tube. The roof 624 may also include an underledge 1202 to provide additional space within housing 604 and/or to abut against a mating feature of housing 604.

The roof 624 in an embodiment also includes recess section 1204, which is configured to align with the tube channel 810 when the door 608 is in the closed position. The recess section 1204 is configured to cradle, contact, or otherwise accept a portion of an external circumference of the IV tube 610. Together, the recess section 1204, the tube window 808, and the tube channel 810 enclose and/or encircle an entire external circumference of an IV tube 610 at the seal section 800.

Figure 13:
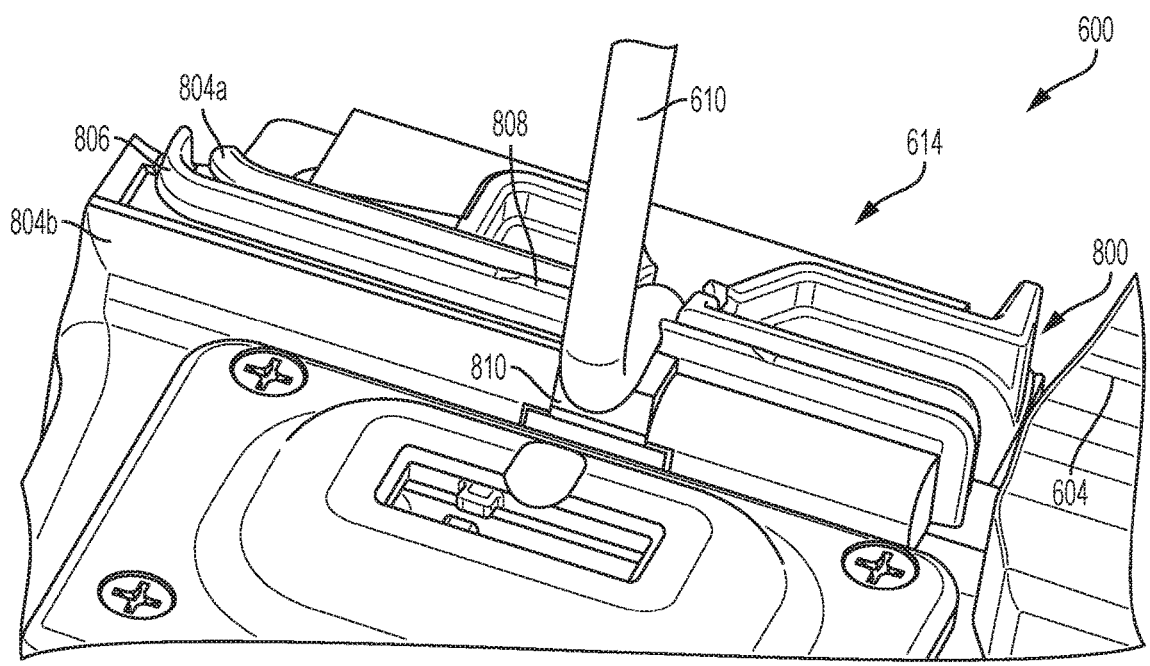
FIGS. 13 and 14 are various views of a top end of the actuation area of the infusion pump of FIGS. 6A, 6B, 7A, and 7B, including a door in the open position and the seal section exposed, according to an example embodiment of the present disclosure.
Figure 14:
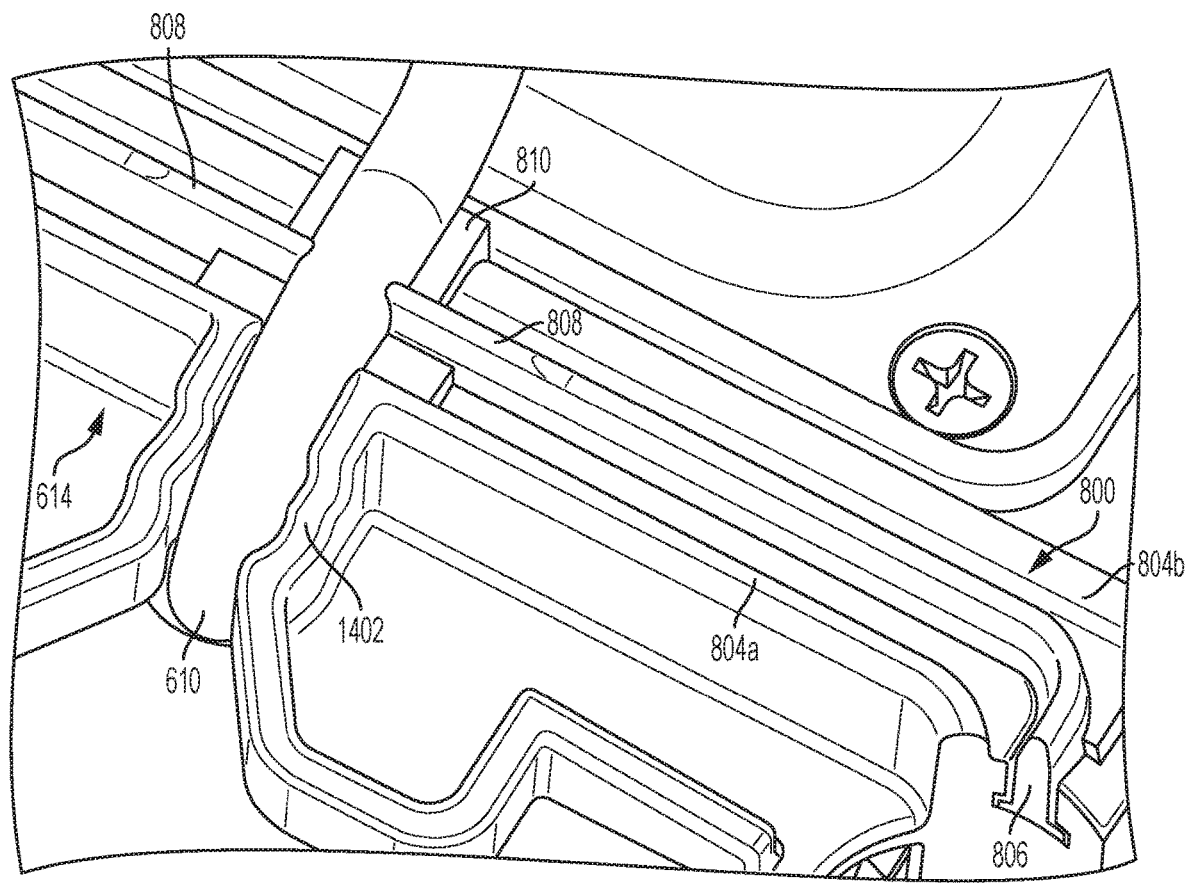

FIGS. 13 and 14 show diagrams of an embodiment of the top end 614 of the actuation area 606 with the door 608 in the open position and the seal section 800 exposed. In FIG. 13, the ridge 804 includes a cutout for the tube channel 810. In other example, the tube channel 810 may be positioned on top of the ridge 804b. As discussed above, the tube channel 810 in an embodiment is configured to cradle or otherwise engage and securely seal the IV tube 610 without substantial compression. FIG. 13 also shows the tube window 808 of the gasket rib 806 engaging the IV tube 610. In addition, FIG. 13 shows the gasket rib 806 extending beyond the ridges 804 and running vertically down the housing 604 adjacent to a gap between an edge of the door 608 and the housing 604 when the door 608 is in the closed position.

FIG. 14 shows a top plan view of an embodiment of the top end 614 of the actuation area 606 including the exposed seal section 800. In this example, the ridge 804a includes a valley that is connected to the gasket rib 806. The valley may enable, for example, the gasket rib 808 to compress and expand slightly when contacted by an underside of the roof 624. The valley may also trap leaked fluid and/or other contaminates that are able to bypass the gasket rib 806 and/or the combination of the recess section 1204, tube channel 810, and the tube window 808 when the door 608 is in the closed position.

FIG. 14 also shows the gasket rib 806 (sectioned) wrapping around towards hinge 612 of the door 608 to seal that section. Altogether, the gasket rib 806 provides a seal in three-dimensions to enclose actuation area 606. This includes providing seals adjacent to edges of the door 608 in the x and y axes in combination with a seal in the z-axis adjacent to the roof 624.

It should be appreciated that the ridge 804a, or at least the edge or lip of the ridge 804a does not include a cutout for the tube channel 810. Instead, the tube channel 810 extends into the valley of the ridge 804a and ends at the raised edge. FIG. 14 shows an embodiment of a tube guidance section 1402, which is connected to and/or integrated with the ridge 804a at the tube channel 810. The tube guidance section 1402 is configured to cradle or otherwise accept the IV tube 610 causing the IV tube to bend for a desired, e.g., vertical, orientation in the actuation area 606. In some embodiments, the tube guidance section 1402 may be dimensioned to contact and provide guidance or a surface for bending the IV tube 610 downward to the actuation area 606. The tube guidance section 1402 includes cascading ridges, which may align with corresponding structure on an underside of the roof 624 to further guide or position the IV tube 610. In some embodiments, the tube guidance section 1402 may relieve stress and/or strain at the bend in the IV tube 610.

Figure 15:
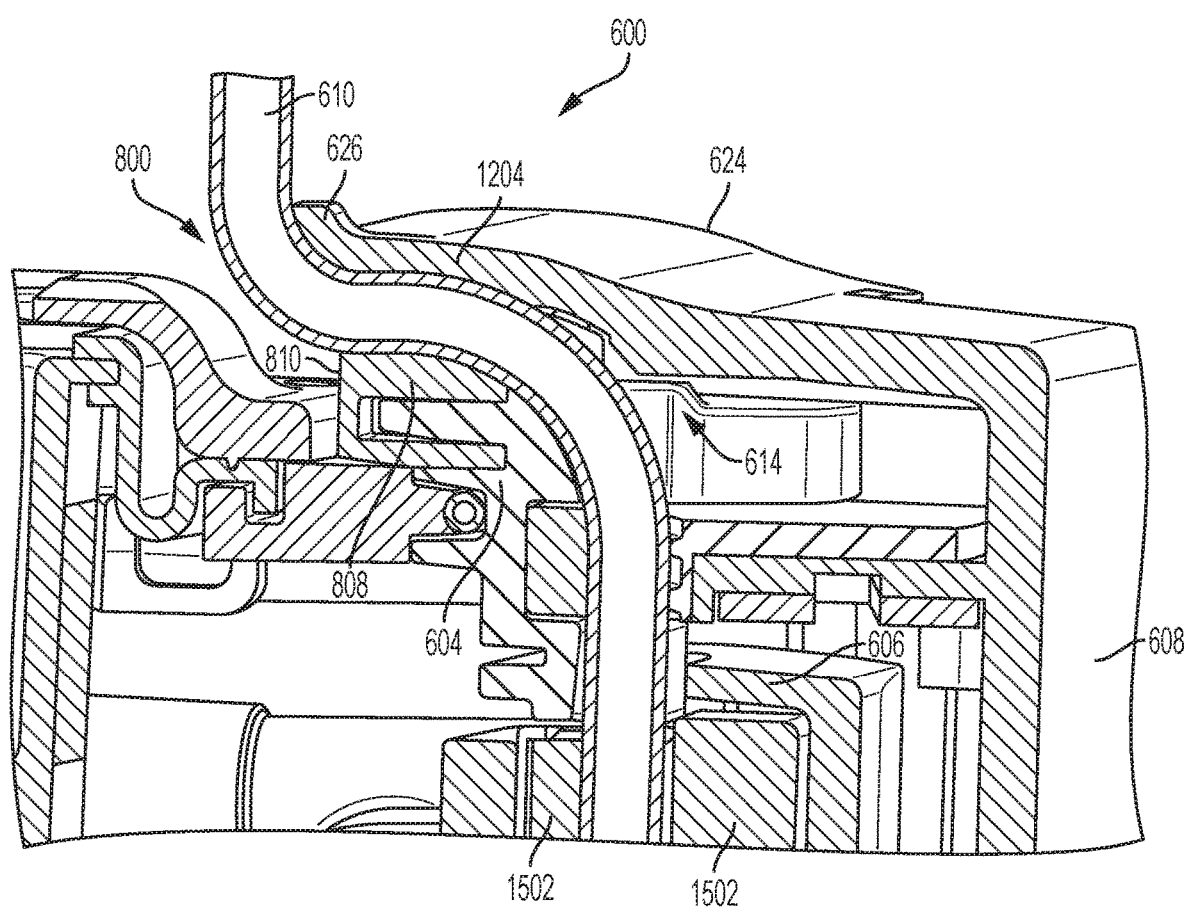
FIG. 15 shows is a perspective, cross-sectional view of a seal section of the infusion pump of FIGS. 6A, 6B, 7A, and 7B, according to an example embodiment of the present disclosure.

FIG. 15 shows a cross-section of an embodiment of the infusion pump 600 at the IV tube 610. As shown, the door 608 encloses the actuator area 606 including actuators 1502. The roof 624 extends or covers the top end 614 of the actuation area 606 and the seal section 800. In the illustrated embodiment, the IV tube 610 is bent from a vertical orientation to a horizontal orientation as the IV tube 610 is received under the roof 624. The bend occurs at the channel relief lip 626. The combination of the tube channel 810, roof recess section 1204, and the tube window 808 encloses the IV tube 610 under the roof 624. The tube channel 810 located inside the door 608 enables the IV tube 610 to be bent in a desired, e.g., vertical, orientation, to permit the tube to be compressed by the actuators 1502 to pump fluid. In the illustrated embodiment, the roof 624 and the seal section 800 provide a barrier preventing contaminates from entering the actuation area 606 while enabling a wider range tolerances between the door 608 and the housing 604. In other words, any gap that may occur between the door 608 and the housing 604 of the infusion pump 600 is protected by the seal section 800, which is positioned just inside the edges of the door.

Roof Embodiments

FIGS. 16 to 24 illustrate various views of the roof 624 of FIG. 12, according to example embodiments of the present disclosure. It should be appreciated that the embodiments illustrated in FIGS. 16 to 24 are only illustrative of possible roof designs. The roof 624 of the door 608 of the infusion pump 600 may comprise any design operable with the seal section 800 to prevent contaminates from entering the actuation area 604.

Figure 16:
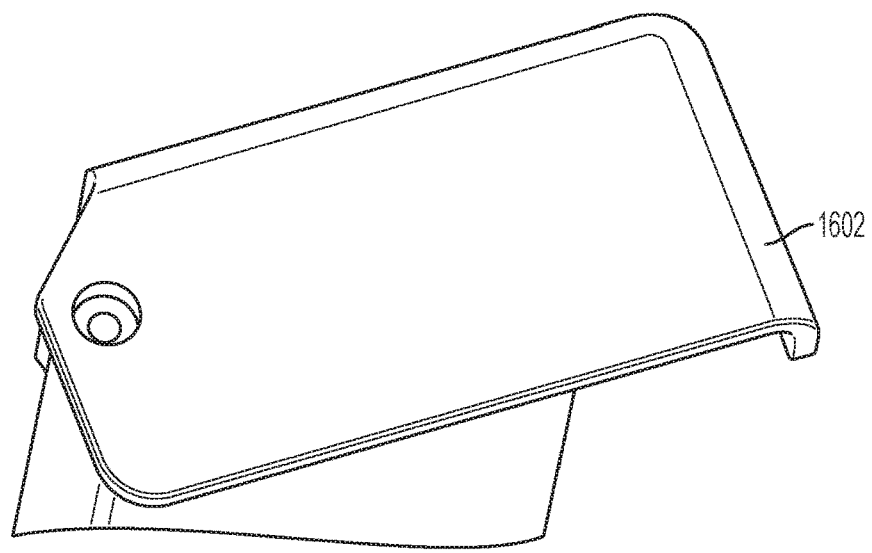
FIGS. 16 to 24 are various views of a roof of FIG. 12, according to example embodiments of the present disclosure.
Figure 17:
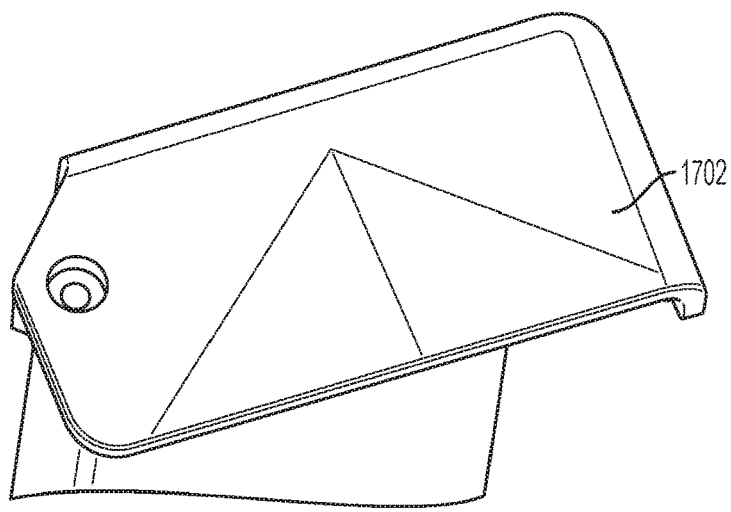
Figure 18:
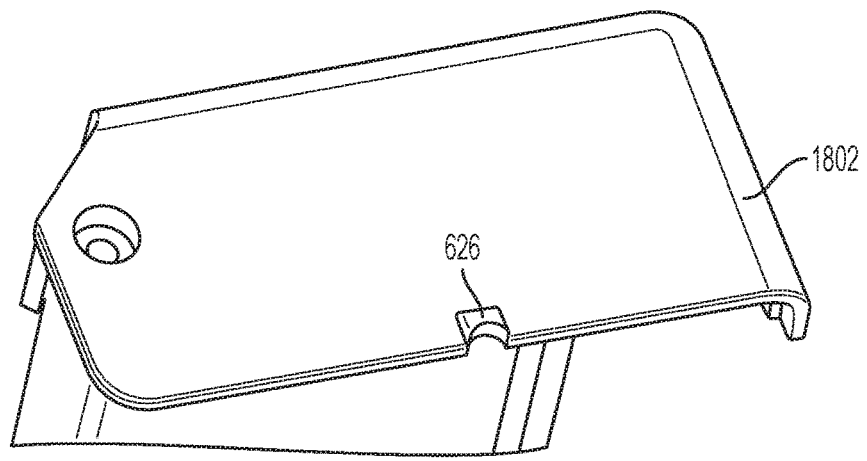

FIGS. 16 to 18 show an example topside of the roof 624. For instance, FIG. 16 shows a perspective top-view of a roof 1602 with a flat surface. FIG. 17 shows a perspective top-view of a roof 1702 with a ridged-shaped surface. Both of the roofs 1602 and 1702 do not include a channel relief lip. In comparison, FIG. 18 shows a perspective top-view of a flat roof 1802 with the channel relief lip 626.

Figure 19:
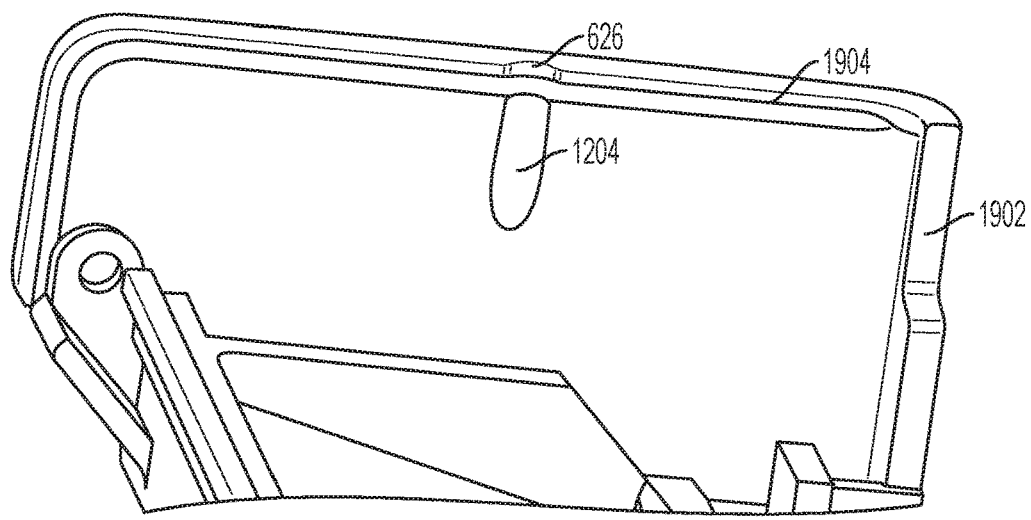
Figure 20:
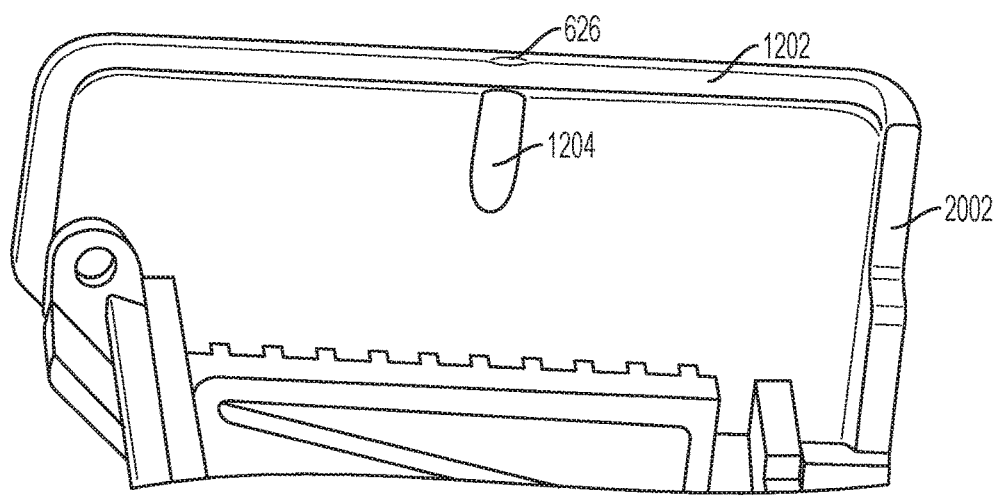

FIGS. 19 to 22 show example bottom sides of the roof 624. For instance, FIG. 19 shows a perspective view of an underside of roof 1902 with an undercut 1904. By comparison, FIG. 20 shows a prospective bottom-view of roof 2002 with underledge 1202. The difference between the undercut 1904 and the underledge 1202 is that the underledge 1202 extends to an edge of the roof 2002 while the undercut 1904 comprises a shallow channel located just inside from an edge of the roof 1902. In addition to being designed to connect to or accommodate features on adjacent housing 604, both the undercut 1904 and the underledge 1202 may be configured to break or partition fluid flow into droplets to ease contamination prevention of the seal section 800.

Figure 21:
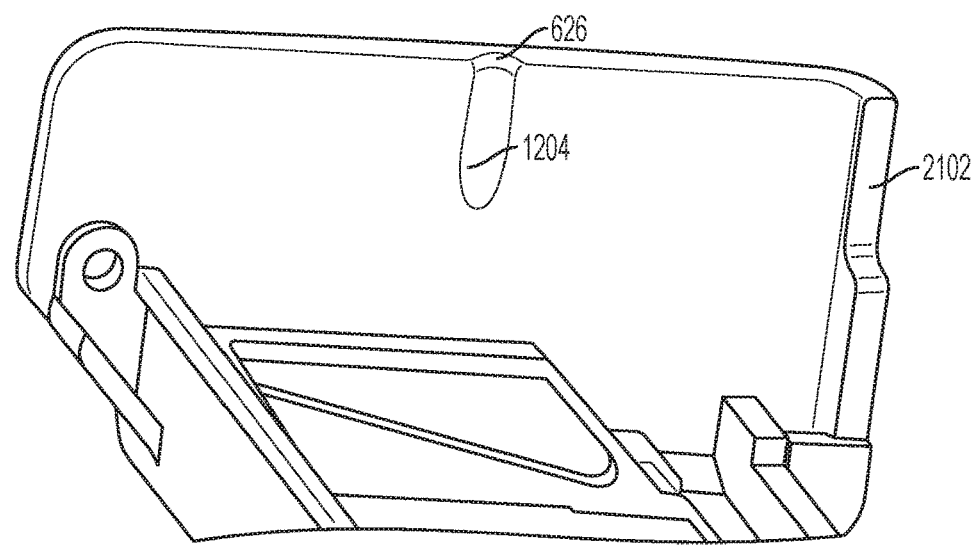

In contrast to FIGS. 19 and 20, FIG. 21 shows a roof 2102 with a flat edge, illustrating that an undercut or underledge is not required. However, FIGS. 19 to 21 show similar recess sections 1204 and channel relief lip 626. In these illustrated examples, the recess sections 1204 have a smooth surface and/or contour. The channel relief lip 626 may also have a smooth surface.

Figure 22:
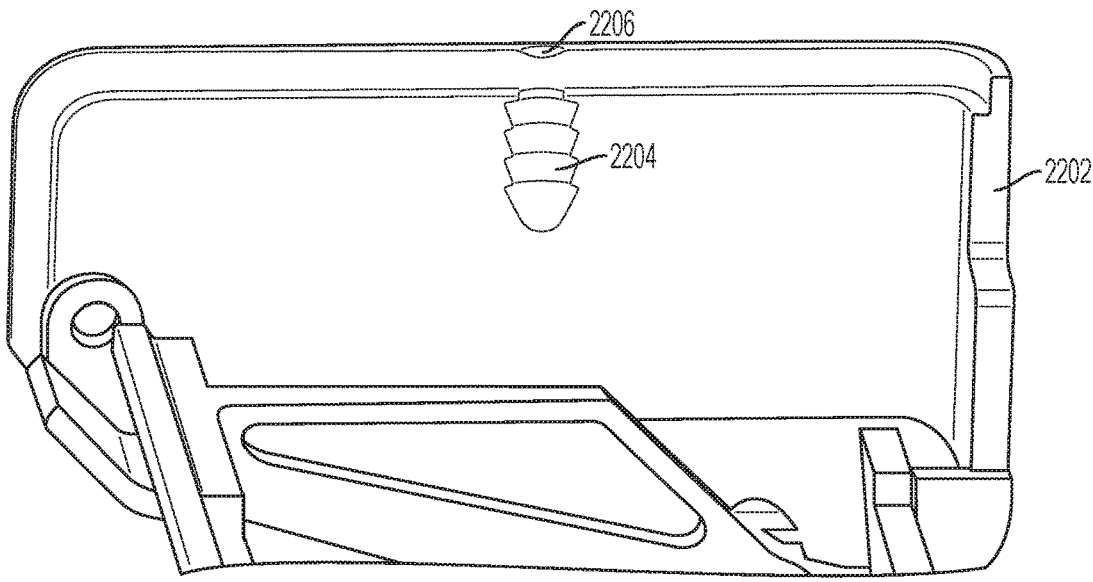

FIG. 22 shows a view of an underside of roof 2202 with a recess section 2204 having a ribbed surface and/or contour. The ribbed surface may improve a seal between the roof 2202 and an IV tube. For example, the ridges of the ribs may depress into IV tube creating a secure connection. However, the gaps between the ridges release compressive stress so that the ridges do not fully compress or occlude the IV tube. The ribs of the recess section 2204 may also provide a grip on IV tube to prevent movement. FIG. 22 accordingly shows that a channel relief lip may also be ribbed.

Figure 23:
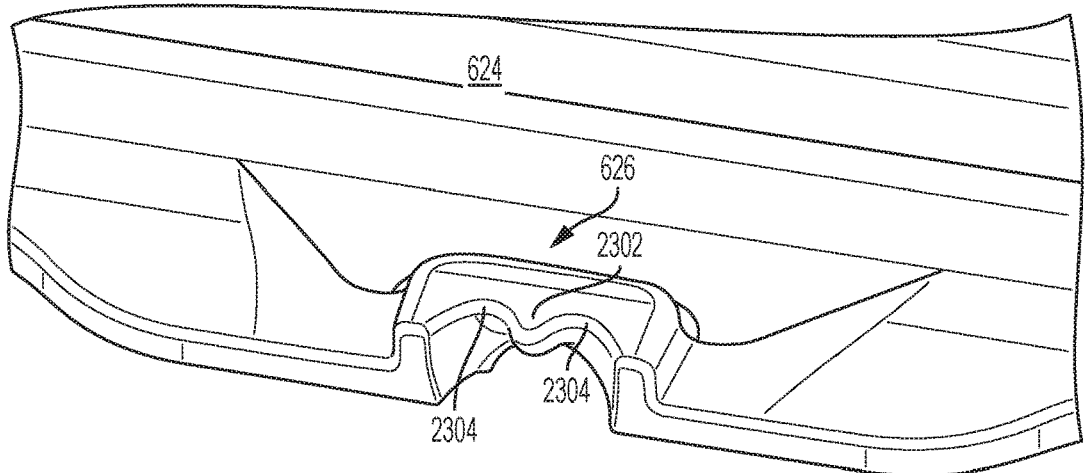
Figure 24:
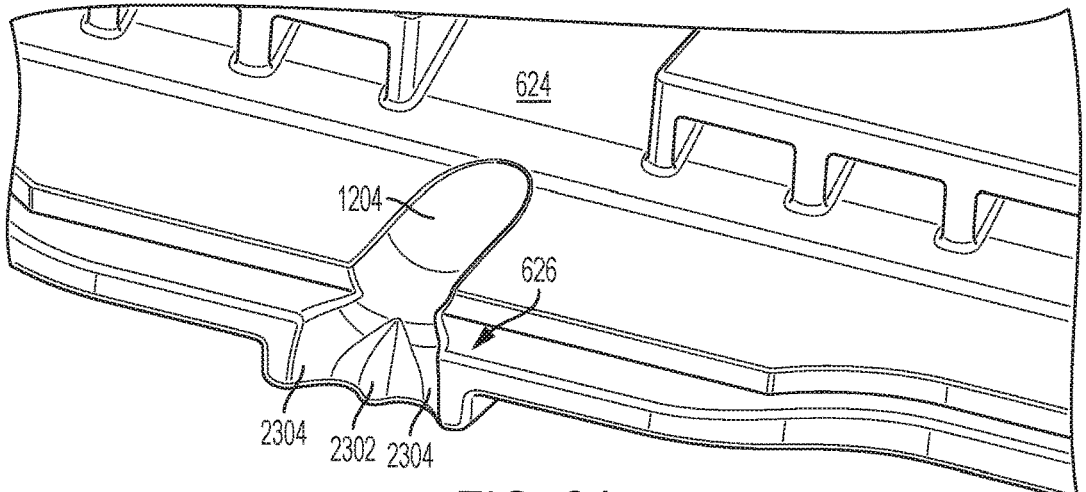

FIGS. 23 and 24 show an embodiment of channel relief lip 626 of FIGS. 6B to 12 and 19 to 22 with a channel rib 2302. FIG. 23 shows a top view of the channel relief lip 626 with channel rib 2302. FIG. 24 shows a bottom view of the channel relief lip 626 with channel rib 2302. Channel rib 2302 includes one or more protrusions within the channel relief lip 626. For instance, while FIGS. 23 and 24 show one protrusion, it should be appreciated that channel relief lip 626 may include two, three, or more channel ribs 2302. As shown in FIG. 24, the channel rib 2302 ends at a start of the recess section 1204, where IV tube typically has a horizontal orientation.

The example channel rib 2302 is configured to prevent an IV tube from compressing and causing a fluid occlusion.

Specifically, the channel rib 2302 causes a bent IV tube to form two or more internal channels in relief lip valleys 2304 adjacent to the rib 2302. In other words the channel rib 2302 is a compression point on an IV tube, whereas the relief lip valleys 2304 provide areas of stress release, thereby preventing a bent IV tube from completely closing.

Seal Section Embodiments

Figure 25:
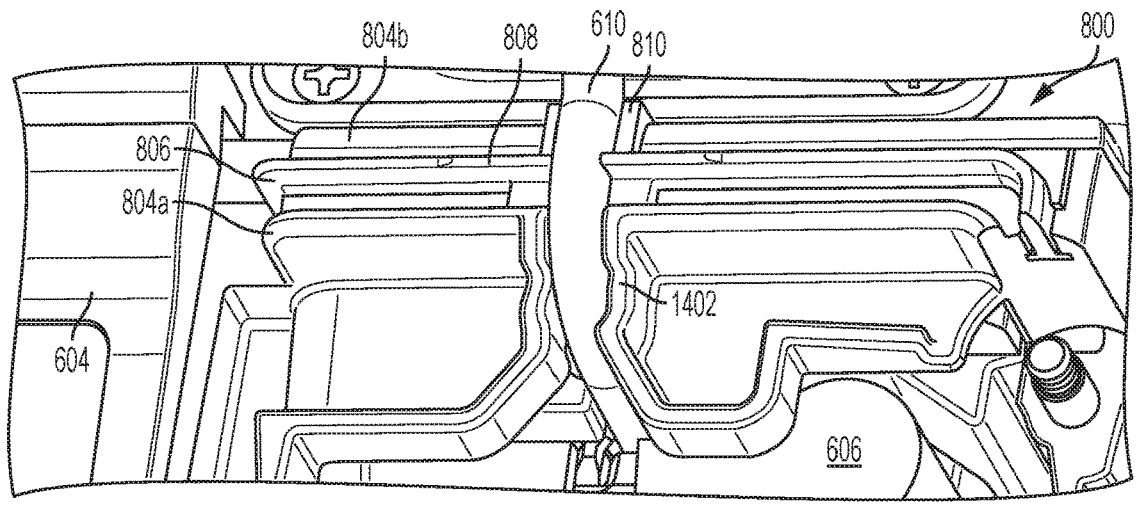
FIGS. 25 to 31 are various views of a seal section of the infusion pump of FIGS. 6A, 6B, 7A, and 7B, according to example embodiments of the present disclosure.

FIGS. 25 to 31 illustrate various views of a seal section 800 of the infusion pump 600 of FIGS. 6A, 6B, 7A, and 7B, according to example embodiments of the present disclosure. The seal sections 800 in the example embodiments of FIGS. 25 to 31 are formed and operate at least substantially similar to the seal sections described above. FIG. 25 shows seal section 800 with gasket rib 806 between ridges 804a and 804b. The gasket rib 806 is connected to or integrated with tube window 808 and tube channel 810, as discussed above.

Figure 26:
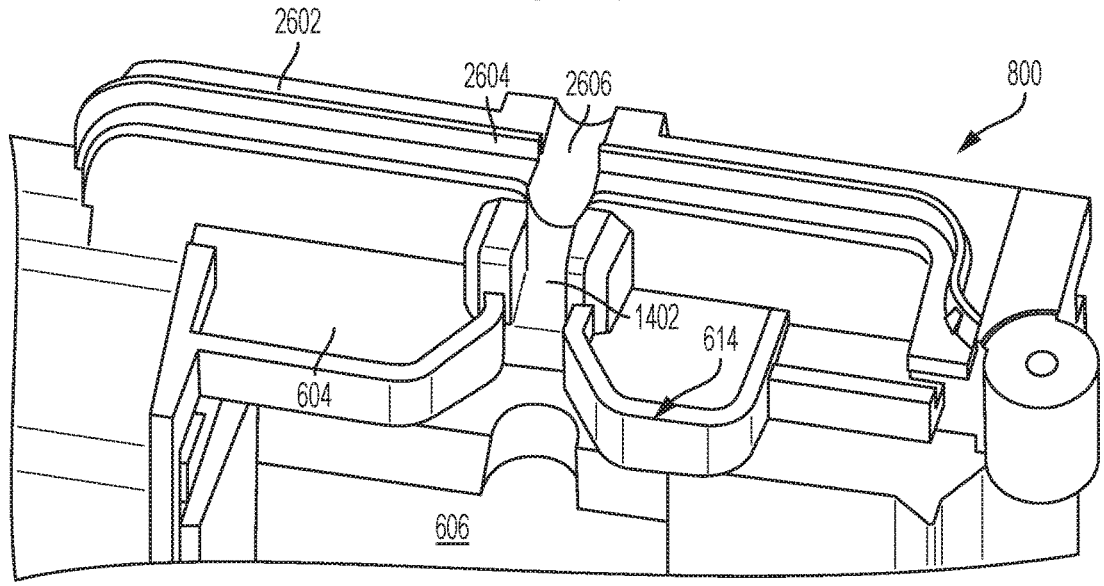

FIG. 26 shows an embodiment of seal section 800 including gasket rib 2602 without ridges 804. In this example, gasket rib 2602 may be connected to housing 604 at a top end 614 of actuation area 606. The connection of gasket rib 2602 to housing 604 may be strong enough such that ridges 804 are not necessary. Gasket rib 2602 includes a tube window 2604 and tube channel 2606. The tube window 2604 may have a same or different height as the gasket rib 2602. As shown in FIG. 26, tube window 2604 and tube channel 2606 are curved to cradle or otherwise accommodate an IV tube. Tube channel 2606 is connected to tube guidance section 1402, which is also configured to cradle or otherwise accommodate an IV tube in addition to support bending of the IV tube.

Figure 27:
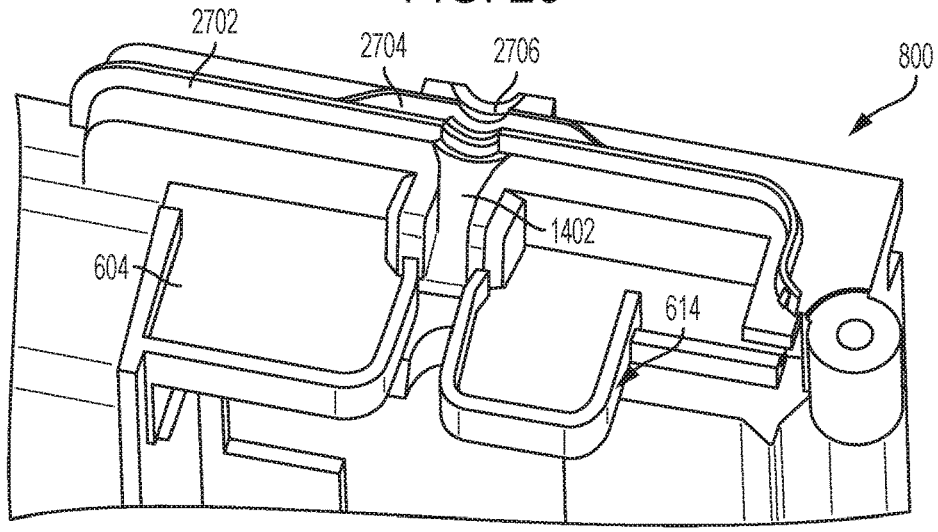

FIG. 27 shows another embodiment of seal section 800 including gasket rib 2702 without ridges 804. In this embodiment, gasket rib 2702 is integrated with and/or formed from a same material as housing 604. For instance, the gasket rib 2702 and housing 604 may include a plastic material. Gasket rib 2702 includes tube window 2704, which includes two ribs in parallel. The ribs are in parallel at a connection point with IV tube at tube channel 2706. Away from tube channel 2706, the second rib is bent to connect to the first rib, which comprises gasket rib 2702. In other embodiments, the second rib may run parallel for an entire length of seal section 800.

In the example of FIG. 27, tube channel 2706 is ribbed. The ribs may enable cradling or gripping of an IV tube without causing compete tube compression and fluid occlusion. The ribs of tube channel 2706 may also trap contaminants before they can enter actuation area 606.

Figure 28:
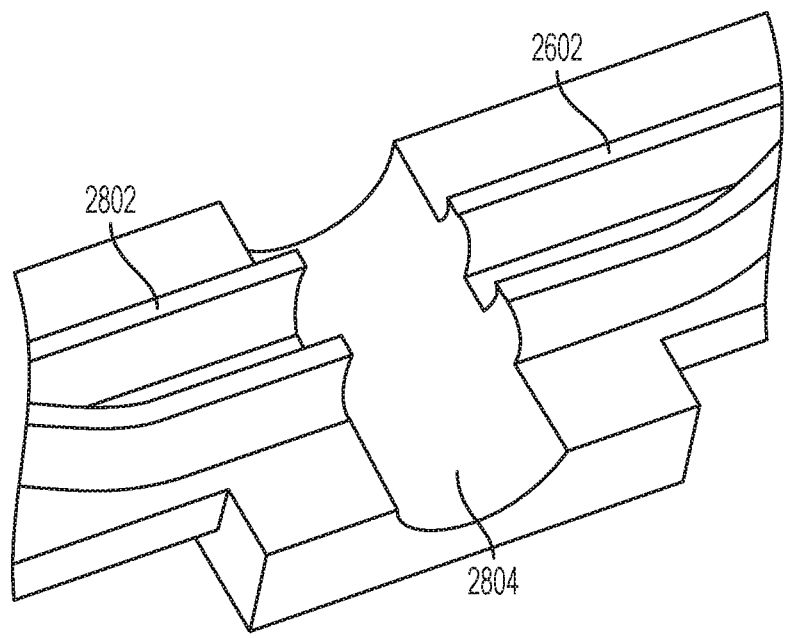
Figure 29:
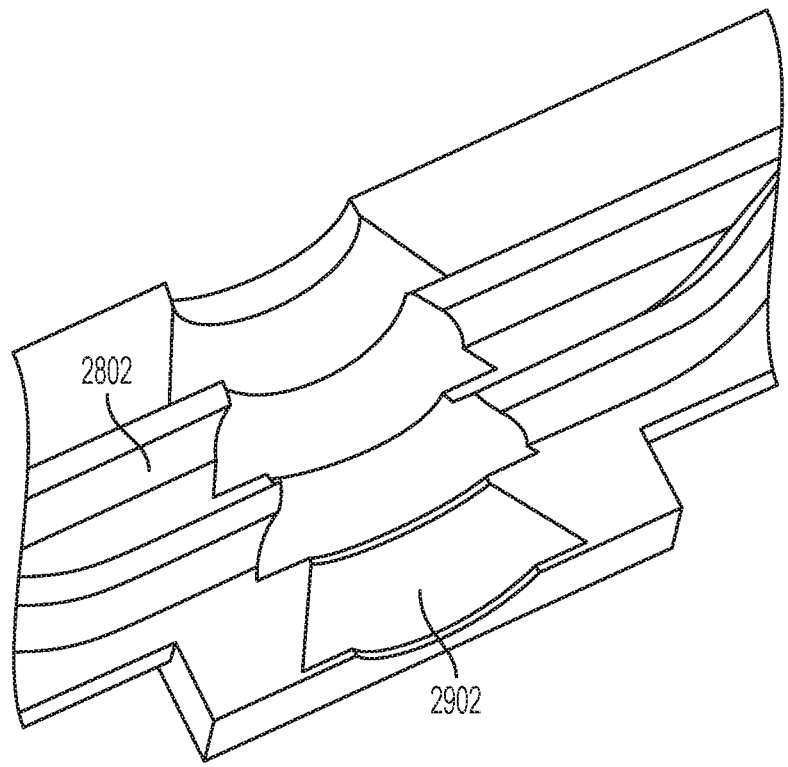
Figure 30:
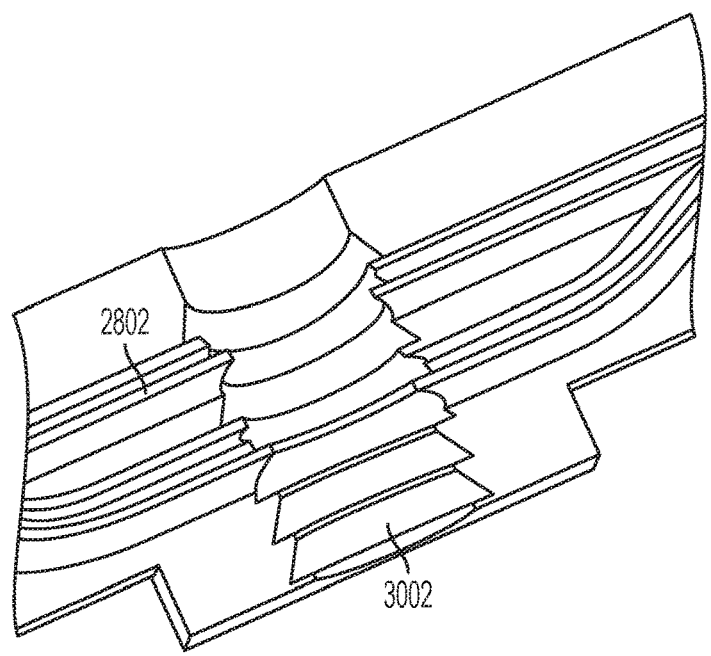

FIGS. 28 to 30 show variations of tube channel 810 of FIGS. 8 to 11, 13 to 15, 25, and 26. In these examples, tube window 2802 includes two parallel ribs. However, in other examples, tube window 2802 may include a single rib, as shown in preceding figures, or include additional ribs in parallel. FIG. 28 shows a tube channel 2804 with a smooth surface. FIG. 29 shows an embodiment where a tube channel 2902 has a course ribbed surface. The ribs of the tube channel 2902 are aligned with the ribs of the tube window 2802 to provide, for example, a more secure connection and/or prevent gaps from forming. In some instances, the ribs of tube window 2802 may have a same or similar width as ribs of tube channel 2902. The ribs of tube channel 2902 may also prevent an IV tube from sliding within tub channel 2902.

FIG. 30 shows a tube channel 3002 with fine or narrow ribs. As shown, ribs of the tube window 2802 have a narrow width to align with the ribs of the tube channel 3002. However, not every rib of tube channel 3002 has a corresponding rib of tube window 2802. The ribs of tube channel 3002 may grip an IV tube to create a secure connection and/or prevent the IV tube from slipping or otherwise moving.

Figure 31:
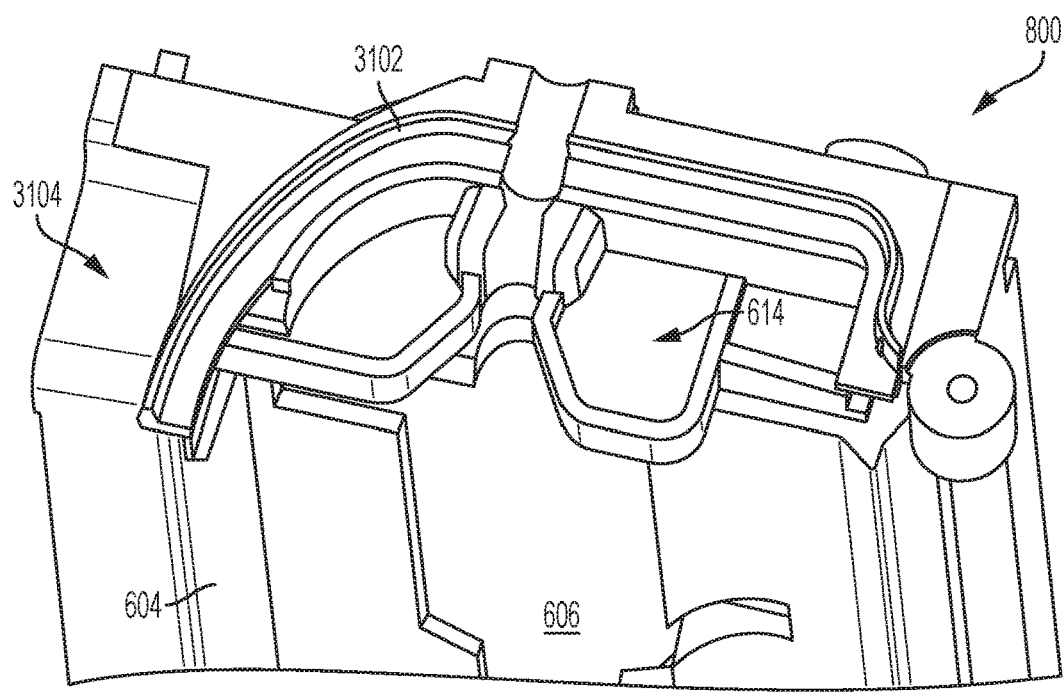

FIG. 31 shows seal section 800 with a gasket rib 3102 that is curved at section 3104 of housing 604. The curvature of the gasket rib 3102 may accommodate or enable door 608 and/or roof 624 to have rounded edges, as discussed below in connection with FIGS. 32 to 36. The gasket rib 3102 may run along housing 604 in a vertical orientation through bottom end 616 of actuation area 606 to provide a seal just inside a vertical edge of door 608.

Roof Shape Embodiments

Figure 32:
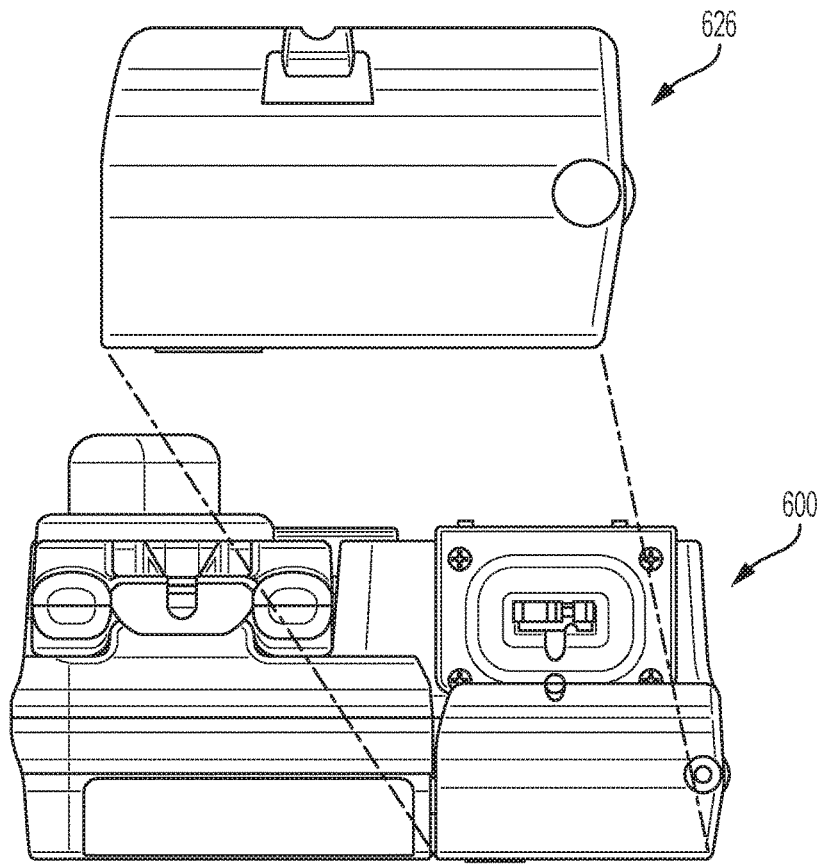
FIGS. 32 to 36 are various views illustrating shape variations of the roof of FIG. 12, according to example embodiments of the present disclosure.
Figure 33:
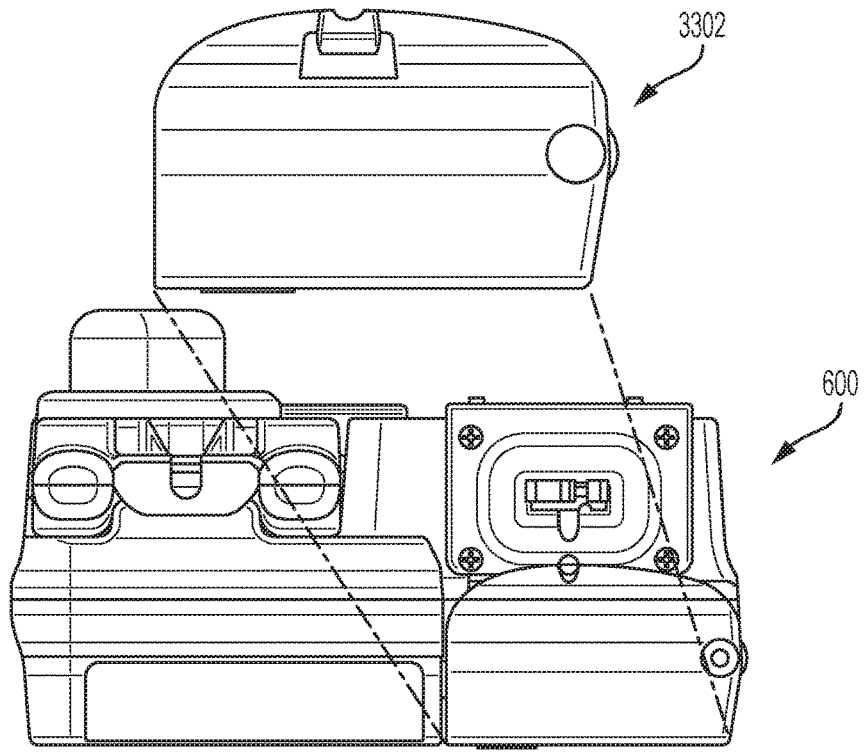

FIGS. 32 to 36 are various views illustrating shape variations of the roof 626 of FIG. 12, according to example embodiments of the present disclosure. The roof in any of the variations may be made of any of the materials discussed herein. FIG. 32 shows a top-down view of roof 626, which has sharper corners. By comparison, FIG. 33 shows a top-down view of roof 3302, which has rounded corners. The rounding or softening of the corners of roof 3302 enables, for example, access to underlying features, such as screws. Roof 3302 of FIG. 32 may be used in conjunction with gasket rib 3102 of FIG. 31.

Figure 34:
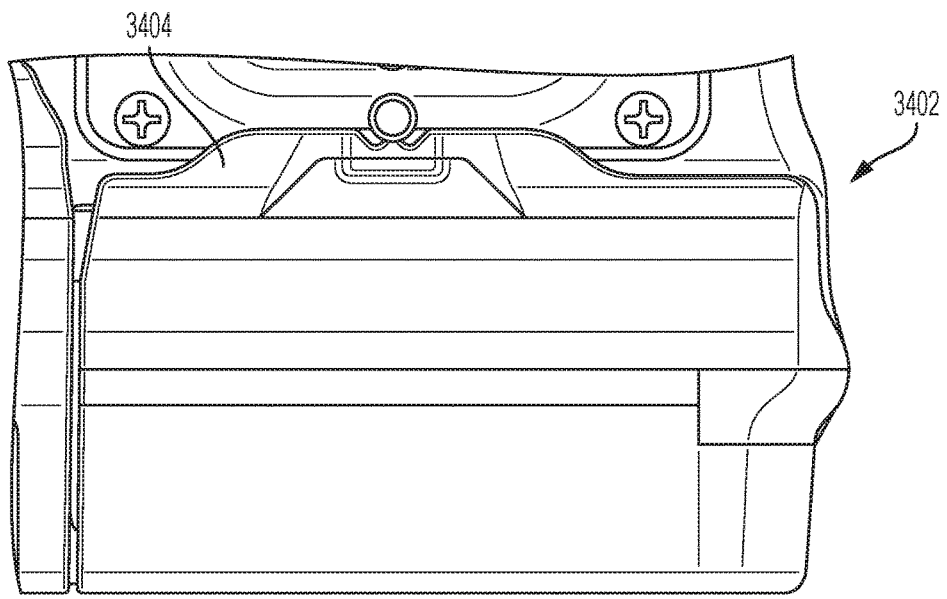
Figure 35:
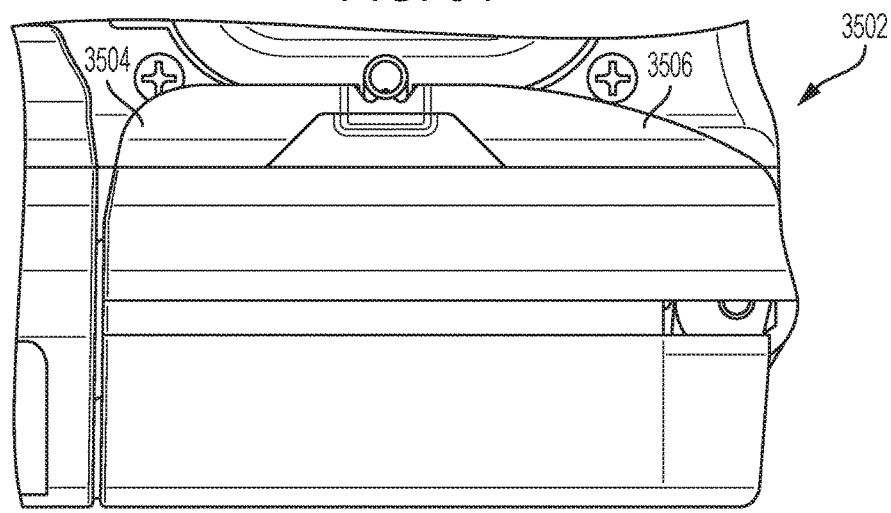
Figure 36:
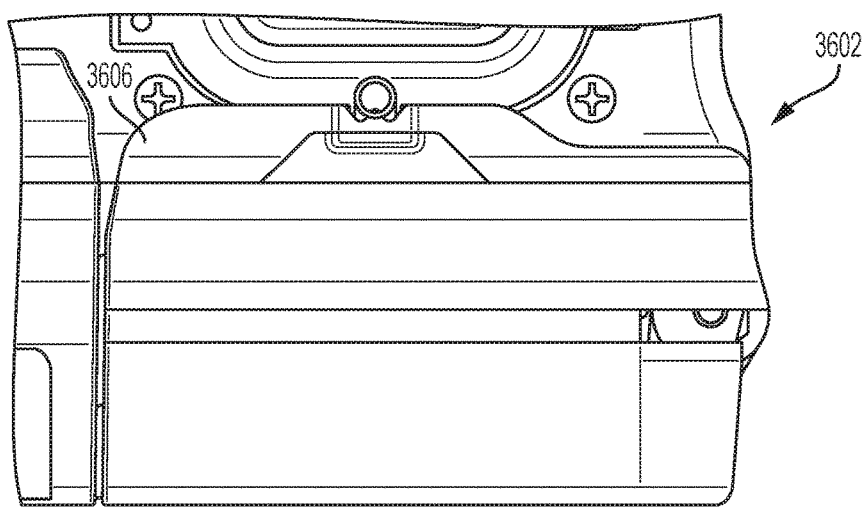

FIGS. 34 to 36 show additional roof variations with rounded edges. For example, FIG. 34 shows roof 3402 with a tab 3404, with rounded edges at the channel relief lip. Similarly, FIG. 36 shows roof 3602 with a tab 3406 that extends to an edge of the roof 3602. FIG. 35 shows roof 3502 with a first corner 3504 and a second corner 3506 with different degrees of roundness. Specifically, the first corner 3504 is relatively sharp while the second corner 3506 has a gradual slope. It should be appreciated that the roof variations shown in FIGS. 34 to 36 are only examples. Other embodiments may have differently shaped roofs based, for example, on features/dimensions of housing 604 and/or how an IV tube is configured to enter an actuation area 606.

CONCLUSION

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. An infusion pump for delivering an intravenous ("IV") fluid comprising:
   a housing having a vertical orientation when the infusion pump is positioned for operation, the housing having a top side configured to engage a horizontal portion of an IV tube; and
   a seal section located along at least the top side of the housing, the seal section including at least one rib positioned along the top side of the housing, the at least one rib extending vertically from the top side and defining a tube window having a width to enable the horizontal portion of the IV tube to pass between edges of the tube window, and a tube channel aligned with the tube window, the tube channel having a horizontal orientation when the infusion pump is positioned for operation, the tube channel being in connection with the tube window and configured to contact a bottom side of the horizontal portion of the IV tube, wherein the at least one rib and the tube channel both include an elastomeric material to enable the at least one rib to create a seal against a door connected to the housing and enable the tube channel to contact the bottom side of the horizontal portion of the IV tube without causing compression or fluid occlusion of the IV tube.

2. The infusion pump of claim 1, further comprising the door connected to the housing, the door including a roof that is configured to sealingly engage the at least one rib positioned along the top side of the housing when the door is closed, the roof including at least one of:
   a recess section configured to align with the tube channel and the tube window when the door is closed, the recess section contacting a top side of the horizontal portion of the IV tube such that the recess section, the tube window, and the tube channel together enclose the horizontal portion of the IV tube, or
   a channel relief lip configured to engage an adjacent vertical portion of the IV tube that is in a vertical orientation when the infusion pump is positioned for operation.

3. The infusion pump of claim 2, wherein the engagement of the horizontal portion of the IV tube by the recess section, the tube window, and the tube channel causes a third portion of the IV tube to bend from the horizontal portion of the IV tube to the vertical portion of the IV tube.

4. The infusion pump of claim 2, wherein the roof further includes a rib that is configured to engage the seal section along at least the top side of the housing.

5. The infusion pump of claim 1, wherein the tube channel includes a surface that is at least one of (i) smooth, or (ii) ribbed.

6. The infusion pump of claim 5, wherein when the tube channel includes the ribbed surface, the ribbed surface is aligned with the at least one rib of the seal section.

7. The infusion pump of claim 1, wherein the at least one rib includes at least one of (i) a single rib, or (ii) at least two ribs in parallel.

8. The infusion pump of claim 7, wherein when the at least one rib includes at least two ribs in parallel, at least one of the parallel ribs has a height that is greater than the other rib or ribs.

9. The infusion pump of claim 1, wherein the at least one rib and the tube channel are molded with the housing.

10. The infusion pump of claim 1, wherein the seal section further includes a tube guidance section connected to the tube channel, the tube guidance section configured to contact a second portion of the IV tube that is adjacent to the horizontal portion of the IV tube, causing the second portion of the IV tube to bend to a vertical orientation.

11. An infusion pump for delivering an intravenous ("IV") fluid comprising:
   a housing having a vertical orientation when the infusion pump is positioned for operation, the housing having a top side configured to engage a horizontal portion of an IV tube; and
   a seal section located along at least the top side of the housing, the seal section including at least one rib positioned along the top side of the housing, the at least one rib extending vertically from the top side and defining a tube window having a width to enable the horizontal portion of the IV tube to pass between edges of the tube window,
   wherein the at least one rib includes an elastomeric material to enable the at least one rib to create a seal against a door connected to the housing,
   wherein the at least one rib includes at least one of (i) a single rib, or (ii) at least two ribs in parallel, and
   wherein when the at least one rib includes at least two ribs in parallel, at least one of the parallel ribs has a height that is greater than the other rib or ribs.

12. The infusion pump of claim 11, wherein the seal section further includes a tube channel that is aligned with the tube window, the tube channel having a horizontal orientation when the infusion pump is positioned for operation, and the tube channel being connected to the tube window and configured to cradle a bottom side of the horizontal portion of the IV tube.

13. The infusion pump of claim 12, further comprising the door connected to the housing, the door including a roof that is configured to sealingly engage the at least one rib positioned along the top side of the housing when the door is closed, the roof including a recess section configured to align with the tube channel and the tube window when the door is closed, the recess section contacting a top side of the horizontal portion of the IV tube such that the recess section, the tube window, and the tube channel together enclose the horizontal portion of the IV tube.

14. The infusion pump of claim 13, wherein the roof further includes a rib that is configured to engage the seal section along at least the top side of the housing.

15. The infusion pump of claim 12, further comprising the door connected to the housing, the door including a roof that is configured to sealingly engage the at least one rib positioned along the top side of the housing when the door is closed, the roof including a channel relief lip configured to engage an adjacent vertical portion of the IV tube that is in a vertical orientation when the infusion pump is positioned for operation.

16. The infusion pump of claim 12, wherein the seal section further includes a tube guidance section connected to the tube channel, the tube guidance section configured to contact a second portion of the IV tube that is adjacent to the horizontal portion of the IV tube, causing the second portion of the IV tube to bend to a vertical orientation.

17. The infusion pump of claim 12, wherein the tube channel includes a surface that is at least one of (i) smooth, or (ii) ribbed.

* * * * *